(12) United States Patent
Stanish et al.

(10) Patent No.: US 6,293,152 B1
(45) Date of Patent: *Sep. 25, 2001

(54) METHOD FOR DETERMINING TWIST POTENTIAL IN WOOD

(75) Inventors: Mark A. Stanish, Seattle; Stan L. Floyd, Enumclaw, both of WA (US); Steven M. Cramer, Lodi, WI (US)

(73) Assignee: Weyerhaeuser Company, Federal Way, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/389,676

(22) Filed: Sep. 2, 1999

Related U.S. Application Data
(60) Provisional application No. 60/098,988, filed on Sep. 2, 1998.

(51) Int. Cl.[7] .......................... G01N 33/46; G01N 29/00; G01R 27/26
(52) U.S. Cl. .............................. 73/597; 73/601; 73/602; 73/432.1; 324/639; 324/663; 356/445; 356/446; 356/237; 250/330; 250/341.8; 250/358.1; 83/72; 83/73; 83/361; 83/365
(58) Field of Search .......................... 73/597, 601, 602, 73/624, 627, 628, 73, 75, 159, 160, 432.1; 324/637–640, 663–664, 683–684, 686–690; 356/364, 371, 376, 383, 384, 445–448, 237, 239; 250/330, 338.1, 341.1, 340, 341.6, 341.8, 358.1, 359.1, 360.1; 144/356, 357, 380; 83/69–73, 360–361, 365, 370, 371; 364/474.13, 474.09, 474.01; 702/35, 38–40, 81, 179–181, 189, 196, 126, 134–136, 155

(56) References Cited

U.S. PATENT DOCUMENTS 3,664,180   5/1972   McDonald et al. .................. 73/67.6
3,805,156   4/1974   Norton et al. ..................... 324/61 R (List continued on next page.)

FOREIGN PATENT DOCUMENTS

91/19194   12/1991   (WO) .

OTHER PUBLICATIONS

Beard, et al., "The Influence of Growth Characteristics on Warp in Two Structural Grades of Southern Pine Lumber," *Forest Prod. J.* 43:51–56 (Jun. 1993).

(List continued on next page.)

*Primary Examiner*—Hezron Williams
*Assistant Examiner*—Rose M. Miller
(74) *Attorney, Agent, or Firm*—Klarquist Sparkman Campbell Leigh & Whinston, LLP

(57) ABSTRACT

A method for determining twist potential of wood is described. One embodiment of the method comprises nondestructively obtaining a grain angle of wood, such as trees or lumber, and then determining twist potential of the wood based on the grain angle. Where the wood comprises lumber, grain angle determinations typically are made on at least one major surface of the lumber. The method typically comprises determining grain angle at at least two measuring locations separated by a predetermined distance, such as at substantially one-foot intervals along the board. The method also can further comprise obtaining at least one fiber dive angle. Particular embodiments of the present invention determine grain angle using infrared radiation, microwave radiation, light energy (such as by using a laser), electricity, ultrasound energy, and combinations thereof. Working embodiments of the method used light energy and ultrasound energy to determine grain angle. For example, a first transmission speed of an ultrasound pulse through the board was determined along a first path and along a second path. Grain angle was then determined by comparing the first and second transmission speeds. Plural grain angles also can be determined using this ultrasound method. Twist potential can be correlated to empirically determined twist angle. The method of the present invention provides can determine twist potential that correlates with empirically determined twist potential with an $R^2$ value of at least 0.50.

33 Claims, 14 Drawing Sheets

U.S. PATENT DOCUMENTS

| | | | |
|---|---|---|---|
| 3,986,268 | 10/1976 | Koppelman | 34/1 |
| 4,201,093 | 5/1980 | Logan | 73/618 |
| 4,500,835 | 2/1985 | Heikkila | 324/58.5 R |
| 4,538,656 | 9/1985 | Wiklund | 144/378 |
| 4,606,645 | 8/1986 | Matthews et al. | 356/446 |
| 4,852,029 | 7/1989 | Pope et al. | 364/556 |
| 4,916,629 | 4/1990 | Bogue et al. | 364/507 |
| 4,926,350 | 5/1990 | Bechtel et al. | 364/550 |
| 4,972,154 | 11/1990 | Bechtel et al. | 324/663 |
| 5,224,381 | 7/1993 | Sandoz et al. | 73/597 |
| 5,357,112 | 10/1994 | Steele et al. | 250/340 |
| 5,394,097 | 2/1995 | Bechtel et al. | 324/687 |
| 5,585,732 | 12/1996 | Steele et al. | 324/663 |
| 5,619,143 | 4/1997 | Stevens et al. | 324/639 |
| 5,654,643 | 8/1997 | Bechtel et al. | 324/687 |
| 5,873,182 | 2/1999 | Fuller | 34/527 |
| 5,960,104 | 8/1999 | Conners et al. | 382/141 |

OTHER PUBLICATIONS

Brazier, "An Assessment of the Incidence and Significance of Spiral Grain in Young Conifer Trees," *Forest Prod. J.*, 308–312, Aug. 1965.

Kliger et al., "Variability in Wood Properties and its Effect on Distortion and Mechanical Properties of Sawn Timber," *Proceedings of the CTIA/UFRO Int'l Wood Quality Workshop*, pp. Vi–15–Vi–22, Aug. 18–22, 1977, Quebec City, Canada.

Wagner et al., "Impact of Log Sweep on Warp in Southern Pine Structural Lumber," *Forest Prod. J.* 45:59–61, Aug. 1994.

Pamphlet for Model 520 Grain Angle Indicator, Metriguard, Inc., Aug. 1998.

Pamphlet for Sylvatest®, Aug. 1998.

Sandoz et al., "Sylvatest Automation in Sawmill.", Aug. 1998.

Sandoz et al., "Log Grading by Ultrasound (BOIPAC Project).", Aug. 1998.

Sandoz et al., "Industrial Realisation of Sylvatest for Timber Grading (completed).", Aug. 1998.

Sandoz et al., "Decay Detection on Living Trees and Grading (FORUS: Ultrasound Testing in Forests).", Aug. 1998.

Sandoz et al., "Analysis of the Acousto–Ultrsonic Signal for Non–Destructive Evaluation of Wood Properties.", Aug. 1998.

Sandoz, "Ultrasonic Solid Wood Valuation in Industrial Applications," $10^{th}$ Int'l Symp. Nondestructive Testing of Wood, Sep. 26–28, 1996, Lausanne CH.

A.N. Faulger's, "Through–Bark Measurement of Grain Direction; Preliminary Results," *Forest Sci.* 15:92–94 (1969).

R.A. Megraw, "Wood Quality Factors in Loblolly Pine," TAPPI Press, Atlanta, GA (1985).

Meylan, B.A., "Cause of High Longitudinal Shrinkage in Wood," Forest Products Journal, 18(4): 75–78 (1968).

Ormarsson, S., "A Finite Element Study of the Shape Stability of Sawn Timber Subjected to Moisture Variations," thesis, Division of Structural Mechanics, Lund Institute of Technology, Lund, Sweden (1995).

Ormarsson, et al., Influence of Annual Ring Orientation on Shape Stability of Sawn Timber, in Quiality Wood Drying Through Process Modeling and Novel Tecnologies, Proceedings of the Fifth International IUFRP Wood Drying Conference (1996), 427–436.

Perstorper et al., "Quality of Timber Products from Norway Spruce," Wood Sci Tech. 29 (1995), 339–352.

Ying, L., et al., "Longitudinal Shrinkage in Fast–Grown Loblolly Pine Plantation Wood," Forest Prod. J. 44(1):58–62, Jan. 1994.

Martensson, A. et al., Application of a Material Model Describing Drying Stresses in Wood, Proceedings of the Fifth International IUFRP Wood Drying Conference (1996), 93–102.

Kifetew, G. et al., "Tangential and Radial Deformation Field Measurements on Wood During Drying," Wood Science and Technology 31 (1997) 35–44.

Pentoney, R.E., "Mechanisms Affecting Tangential vs. Radial Shrinkage," Journal of FPRS, 27–32, Jun. 1953.

Balodis, V., "Influence of Grain Angle on Twist In Seasoned Boards," Wood Science, vol. 5, No. 1, Jul. 1972.

Taylor, F.W., et al., "Impact of Log Sweep on Warp in Douglas–Fir Structural Lumber," Forest Products Journal, vol. 46, No. 9, 53–56, Sep. 1996.

Simpson, William T., et al., "Mechanism of Crook Development in Lumber During Drying," Wood and Fiber Science, 16(4), pp. 523–536, Oct. 1984.

McAlister, Robert H., "Shrinkage of Juvenile and Mature Wood of Loblolly Pine from Three Locations," Forest Products Journal, vol. 42, No. 7/8, 25–28, Jul. 1992.

Barber, N.F., et al., "The Anisotropic Shrinkage of Wood," Bd. 18 (1964) H. 5, 146–156.

Tang, R.C., et al. "Investigation of Anisotropic Shrinkage of Isolated Softwood Tracheids with Scanning Electron Microscope, Part I: Longitudinal Shrinkage," Wood Science, vol. 8, No. 1, 415–424, Jul. 1975.

Walker, J.C.F, et al., "Primary Wood Processing," (1993; Chapman & Hall) 94–120.

Hsu, N.N., et al., "Distortion and Internal Stresses in Lumber Due to Anisotropic Shrinkage," Wood Science, vol. 7, No. 4, 298–307, Apr. 1975.

Fridley, Kenneth J., et al., "Modelling Three–Dimensional Distortion of Wood Due to Ansiotropic Shrinkage," Mathl. Comput. modelling vol. 17, No. 9, pp. 23–30 (1993).

Irudayaraj, J. et al., "Stress Analysis of Viscoelastic Materials During Drying," Technology, 11(5), 901–927 (1993).

Sandland, K.M., "Stress and Strain in Drying Wood," Norwegian Institute of Wood Technology, Mar. 1996.

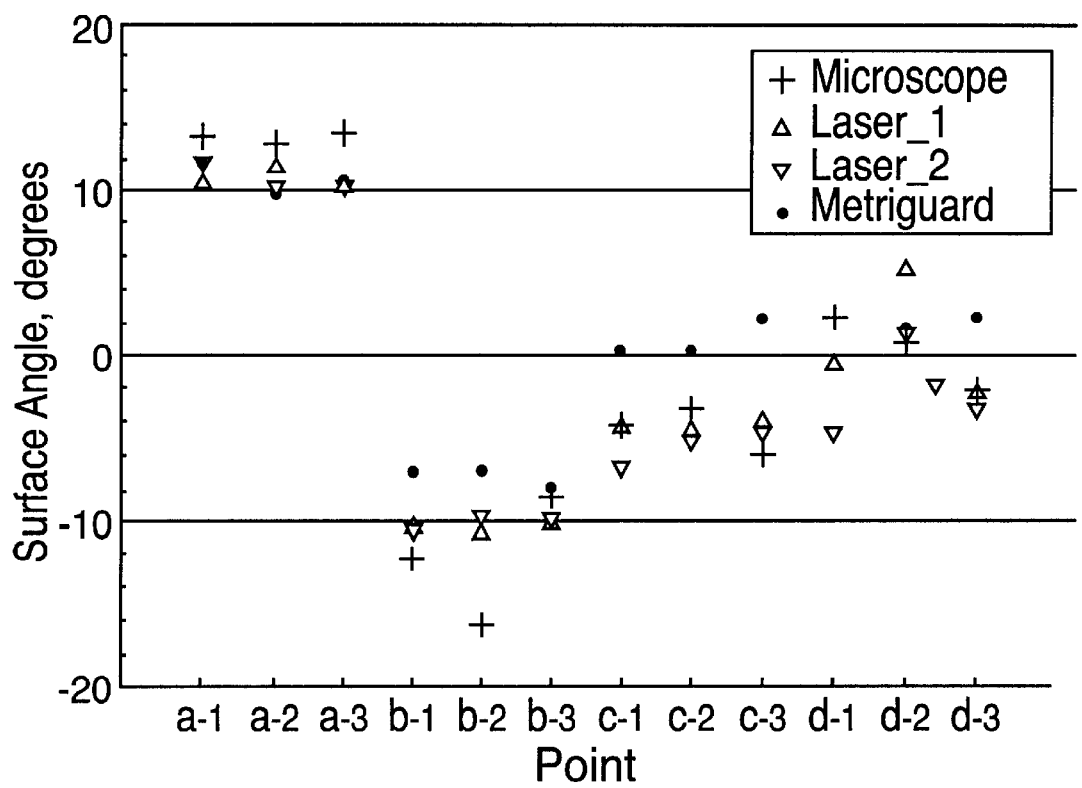

8-ft. 2X4 SPF (0.9" twist)

8-ft. 2X4 SPF

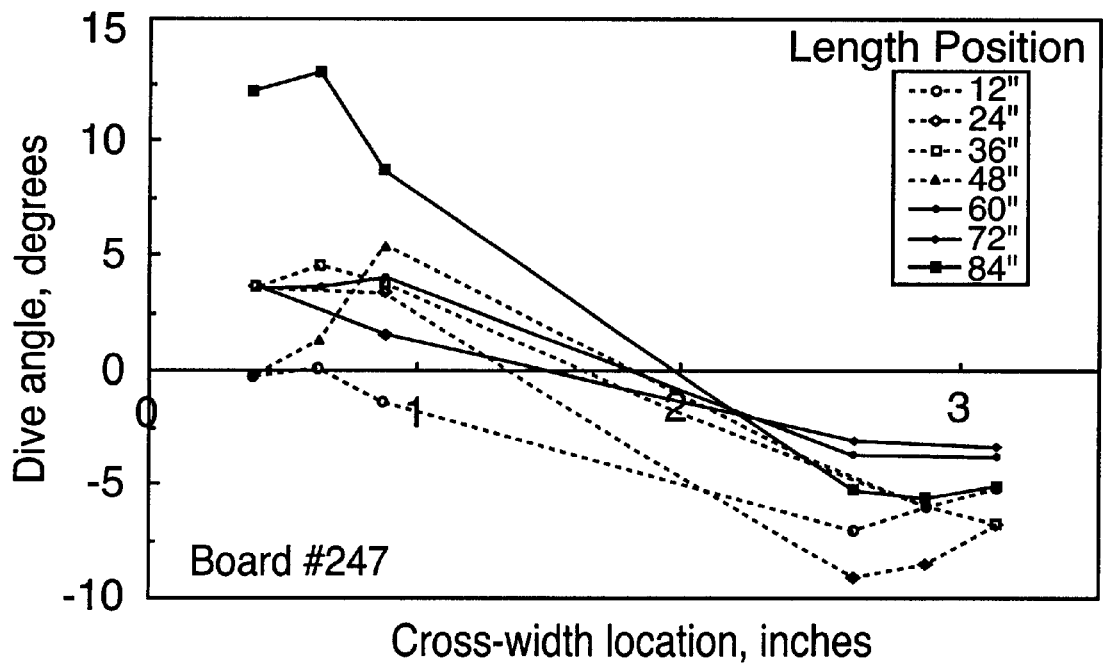

Diagonal Ultrasound Scans

Grain angle →
Ultrasound path - - - -

Zero dive angle

Diagonal Ultrasound Scans

Grain angle →
Ultrasound path - - - -

Non-zero dive angle

METHOD FOR DETERMINING TWIST POTENTIAL IN WOOD

CROSS REFERENCE TO RELATED APPLICATION

This application claims priority from co-pending U.S. provisional patent application No. 60/098,988, filed on Sep. 2, 1998, which is incorporated herein by reference.

A CD-ROM containing a computer program listing appendix has been submitted and is incorporated herein by reference. The CD-ROM contains a single ASCII text file named "DIMENS.txt," created on 23 May 2001, 28 KB in size.

FIELD

The present invention relates to a method for determining warp potential, such as twist potential, in wood—including, without limitation, trees, logs, processed logs, lumber, and manufactured wood products.

BACKGROUND

Warp stability of lumber and wood products is an increasingly important consideration. Three types of warp, known as crook, bow, and cup, can be traced to differential length change within a board. FIG. 2 of Perstorper et al., *Quality of timber products from Norway spruce,* WOOD SCI. TECH. 29 (1995), 339–352, incorporated by reference herein, illustrates different types of warp. Crook refers to in-plane, facewise curvature of wood relative to a longitudinal axis. Bow also refers to in-plane facewise curvature relative to a longitudinal axis. Crook and bow are closely related and differ primarily according to the planar surface used to define the warp. Crook refers to in-plane, facewise curvature of wood relative to a length axis. Twist, another type of warp, refers to a rotational instability about an axis of wood (usually the longitudinal axis). Twist appears to be associated with varying grain angle patterns (Brazier). Warp tendency apparently is influenced by a myriad of factors (see Table 1).

TABLE 1

| Factor | Reference Authors |
| --- | --- |
| Compression wood | Ying, Kretschmann, Bendtsen |
| Drying stresses | Martensson and Svensson |
| Earlywood vs. late wood | Kifetew, Lindberg, Wiklund; Pentoney |
| grain angle | Balodis, Ormarsson |
| log sweep | Taylor and Wagner |
| Longitudinal shrinkage | Ormarsson; Simpson and Gerhardt; Ying, Kretschmann, Bendtsen; McAlister and Clark |
| Microfibril angle | Barber and Meylan; Tang and Smith; Ying, Kretschmann, Bendtsen; Walker |
| Moisture content gradients | Simpson and Gerhardt |
| radial and tangential shrinkages | Kifetew, Lindberg, Wiklund; Meylan |
| Specific gravity | Pentoney; Ying, Kretschmann, Bendtsen |
| stress and strain | Ormarsson; Sandland; Hsu and Tang; Fridley and Tang; Simpson and Gerhardt, Irudayaraj and Haghighi |

Dimensional and warp stability have always been valued attributes. Furthermore, new products emerging from dimension lumber, such as premium-grade joists and studs, require superior dimensional and warp stability performance. The ability to quantify warp potential of wood products would enhance the capability of the forest products industry to service these important markets.

Moreover, inefficient processing of raw timber and lumber wastes tremendous forest resources. Lumber warp reduces product grade and product value. Additionally, warp-prone lumber and lumber products perform poorly in uses or environments unsuitable for warp-prone wood. Millions of dollars are wasted every year because no method exists for efficiently and accurately detecting warp-prone lumber.

If warp-prone wood could be nondestructively identified during or prior to processing and product placement, processing raw timber and lumber into wood products would become more efficient. Raw logs could be culled prior to manufacturing, and wood-products manufacturing processes could be altered to direct raw lumber to various end products according to quality and value. For example, warp-prone trees could be identified while standing in forests or after cutting, and processed into products where warp is an irrelevant consideration (e.g. paper products, chipping, etc.). Green warp-prone lumber could be identified at the mill, separated, and kiln-dried using special warp-reducing techniques (e.g. rapid-drying, high-heat drying, final steaming, restraint-drying, etc.). Lumber having low warp potential could be dried using simpler and more economical methods.

Natural resources are unnecessarily wasted by using certain types of wood in inappropriate applications. If warp tendency of raw logs could be predicted, then warp-prone logs could be processed differently. For example, warp-prone logs could be cut into lumber with cuts being coordinated to reduce warp. The orientation of boards taken from certain logs could be altered to reduce warp, or the thickness of the lumber could be varied, since thicker lumber generally warps less. Alternatively, warp-prone logs could be culled and processed for specific uses (e.g. chipped, lumber for pallets, etc.). Lumber cut from warp-prone logs also could be specially processed (e.g. special kiln drying techniques) or used in selected applications (e.g. relative constant moisture applications).

Additionally, warp-prone lumber could be identified for use in only certain applications. For example, exterior window and door casings experience fluctuating moisture and temperature conditions during use. Warp prone lumber, even if initially straight when dried, could warp in such changing environments. Consequently, if warp-prone lumber could be identified, its use in warp-inducing environments could be avoided. Extremely warp-prone wood may be suitable only for uses where warping is not a significant problem (e.g. for pallets, landscape applications, etc.). In such cases, warp-prone green lumber could be processed without expensive drying techniques.

Warp stability has been studied from both the experimental and theoretical viewpoints. For example, earlier studies explored the links between drying warp and certain lumber characteristics, such as knots, slope-of-grain, and juvenile-wood content [Beard, J., et al., *The influence of growth characteristics on warp in two structural grades of southern pine lumber,* 43 FOREST PROD. J. 6, 51 (June 1993); Balodis, V., *Influence of Grain Angle on Twist in Seasoned Boards,* 5 WOOD SCIENCE 44–50 (1972)]. While some relationships were discovered, no commercially viable processes for detecting warp apparently have been developed.

Others have attempted to mathematically model the mechanical phenomena that govern warp instability. A general approach considers elastic, shrinkage, creep, and mechanosorptive elements, including their anisotropic variability and temperature dependence. Such models are complicated. See, e.g., Ormarsson (1995).

Matthews et al's U.S. Pat. No. 4,606,645, which is incorporated herein by reference, describes measuring fiber angle in a fibrous solid material relative to three mutually orthogonal reference axes. The '645 patent is understood to teach the measuring and analysis of light reflected from a wood sample to determine the grain angle of the sample. These measurements are then understood to be used in evaluating the strength of the wood. This reference is not understood to relate to determining warp potential of wood.

Kliger et al. teaches a destructive method for analyzing a board. Longitudinal shrinkage was determined by cutting sticks from a piece of lumber, averaging the shrinkage of each stick to determine a single value for longitudinal shrinkage, and modeling crook. Kliger teaches only a fairly approximate method for modeling crook. Kliger's method also depends on destroying the wood piece to determine crook. Furthermore, the authors employed a model which specified only a single radius of curvature whereas warp in wood can occur about more than one radius of curvature.

A practical and accurate method for predicting crook and bow has, despite extensive efforts, not been developed. Additionally, the amount of information which must be known to predict warp has proved daunting.

SUMMARY

A method for determining twist potential of wood is described which addresses the problems identified above. One embodiment of the method comprises obtaining a grain angle of wood, such as trees or lumber, and then determining twist potential of the wood based on the grain angle. A preferred embodiment comprises indirectly and/or nondestructively determining a grain angle. The method can comprise obtaining grain angle information from a third party, and then determining twist potential, but more likely involves actually measuring at least one grain angle, and typically comprises measuring plural grain angles, to determine twist potential. Where the wood comprises lumber, grain angle determinations usually are made on at least one planar surface of the lumber. The method typically comprises determining grain angle at least two measuring locations separated by a predetermined distance, such as at substantially one-foot intervals along the board. The method also can further comprise obtaining at least one fiber dive angle.

Particular embodiments of the present invention determine grain angle using electromagnetic energy (e.g., infrared radiation, microwave radiation, light energy, such as by using a laser, electricity), acoustic energy (such as ultrasound energy), and combinations thereof. For example, working embodiments of the method have used ultrasound energy to determine grain angle. A first transmission speed of an ultrasound pulse through the board was determined along a first path and along a second path. Grain angle was then determined by comparing the first and second transmission speeds. Plural grain angles also can be determined using this ultrasound method.

Twist potential can be correlated to measured twist. The method of the present invention determines twist potential that correlates with measured twist with an $R^2$ value of at least 0.5 to about 0.8, and preferably at least about 0.6, with a varying moisture content of from about 5% to about 20%.

A person of ordinary skill in the art will recognize that the method described herein for determining twist potential can be automated. For example, the method for determining grain angle can be done using a computer.

Another embodiment of the present invention for indirectly and/or nondestructively determining twist potential in wood comprises analyzing energy which has been imparted to a piece of wood to determine at least one grain angle, and then determining twist potential of the piece of wood from the at least one grain angle. Electromagnetic and/or acoustic energy can be used to determine grain angle, with working embodiments generally using light energy, such as might be supplied by a laser, or ultrasound energy. Grain angles typically are determined at predetermined intervals along the wood, generally at regularly spaced intervals along the wood, such as substantially one-foot intervals.

Still another embodiment of the invention for nondestructively determining twist potential of wood comprises obtaining grain angles of wood at plural measuring locations along the wood, and determining twist potential of the wood based on the grain angles. Twist potential is determined using a model, such as the formula: Twist potential=$K[\overline{SA_1}-\overline{SA_2}]$.

BRIEF DESCRIPTION OF THE DRAWINGS

FIG. 3 illustrates grain angle measurements taken by a variety of devices.

FIG. 7 illustrates a dive angle profile for another twisted piece of wood.

DETAILED DESCRIPTION

A. Introduction

Twist refers to a rotational distortion of a piece of wood about an axis, such as the length axis of a piece of lumber. Spiral grain is the alignment of wood tissues, particularly tracheids and fibers, at an angle relative to the length axis of the stem (Brazier). The term "grain angle" refers to the alignment of wood tissues relative to some specified axis and includes spiral grain as well as other types of grain angle alignments. For example, diving grain (another type of grain angle) occurs when fiber direction is not parallel to the length axis of a piece of lumber, but is either angled upward or downward in reference to the plane defining at least one face of the lumber, if the lumber is rectangular in cross-section (see Matthews et al.'s U.S. Pat. No. 4,606,645).

The present invention provides a method for predicting what twist will occur in a piece of wood. The invention comprises (1) obtaining at least one grain angle measurement of wood, and (2) determining twist potential of the wood based on the at least one grain angle.

Determining twist potential provides a basis for predicting what actual twist will occur during drying or during cycles of drying and wetting (such as seasonal cycles). Once twist potential is determined, twist can be predicted according to the particular characteristics of drying such as drying time, extent, temperature, particular methods, etc. For example, if the piece will be quickly dried over a few days from 30% moisture content (MC) to 12% moisture content (MC), predicted twist can be established using the determined twist potential for the piece.

B. Types of Wood

Any type of wood may be used in practicing the present invention. For example, the method may be used on standing trees growing in a forest. Grain angles of standing trees may be determined by the method of Foulger, A. N., *Through-Bark Measurement of Grain Direction; Preliminary Results,* FOREST SCIENCE, 15(1):92–94 (1969). Twist potential can then be determined from these grain angle measurements.

The method also may be practiced on logs on-site immediately after harvesting, during transport, at a mill, or anywhere during the production process. The method also may be practiced on lumber, including green lumber, at the mill or any other location in the production process. The present invention also encompasses silviculture practices (such as selective harvesting and thinning) and wood product manufacturing processes where decisions regarding the use or destination of wood are made after determining the twist potential of the wood.

C. Measuring Grain Angle

1. Types of Energy and Devices

Grain angle can be measured using a variety of methods, and any device and method suitable for measuring grain angle in wood may be used. As described below, devices are commercially available that can be adapted for measuring grain angle in accordance with the method of the present invention.

Figure 1:
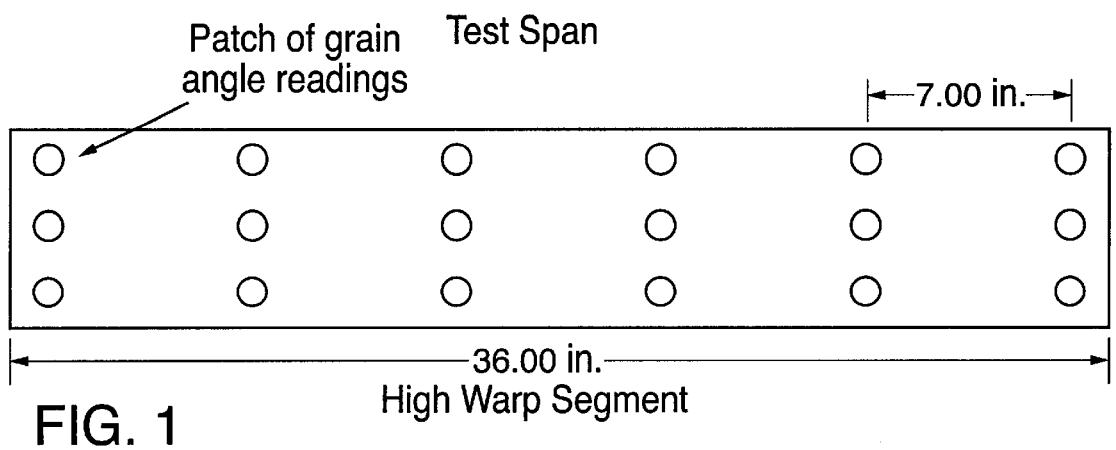
FIG. 1 illustrates a data grid for gathering grain angles.
Figure 2:
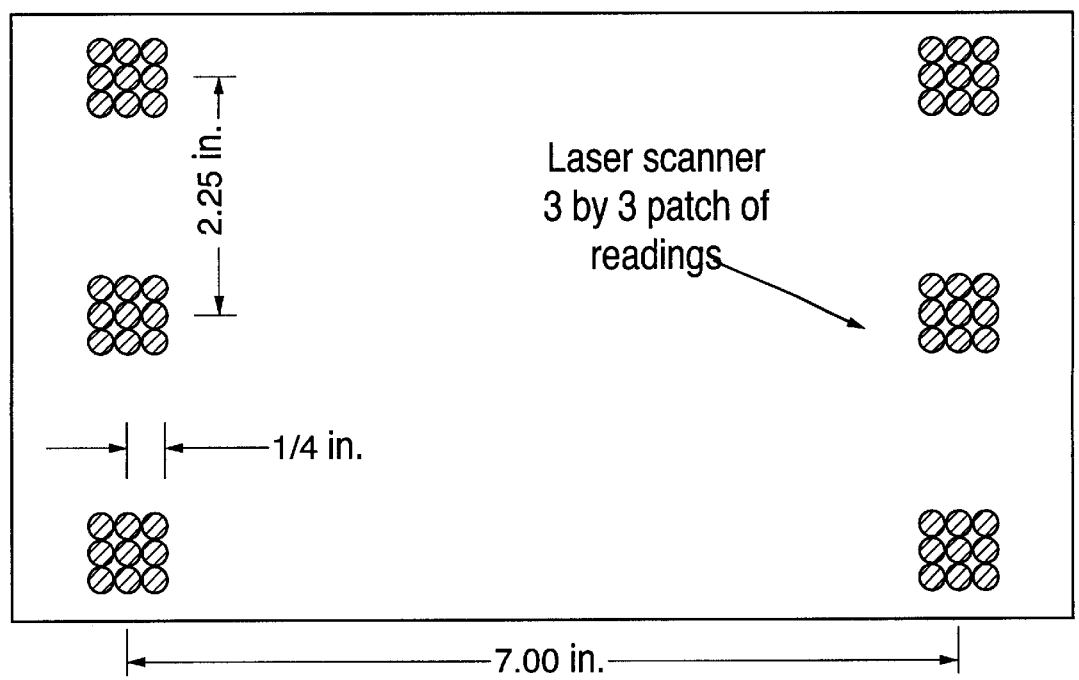
FIG. 2 illustrates 3-by-3 data patches for gathering grain angles.
Figure 4A:
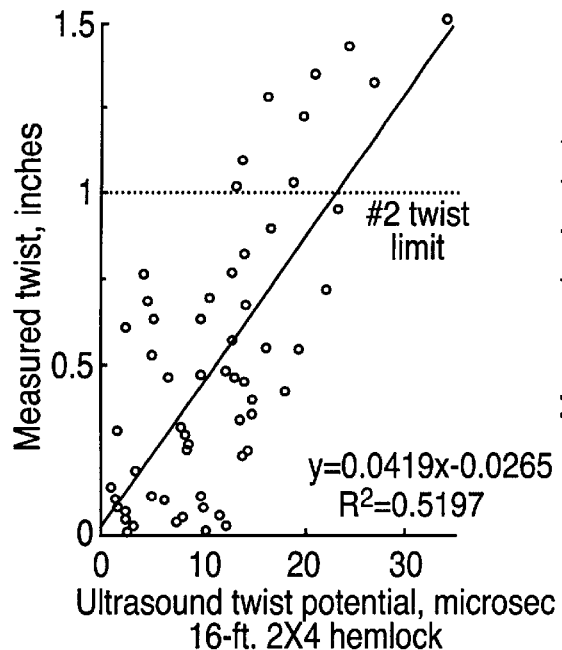
FIG. 4 illustrates the correlation between determined twist potential and measured twist.
Figure 4B:
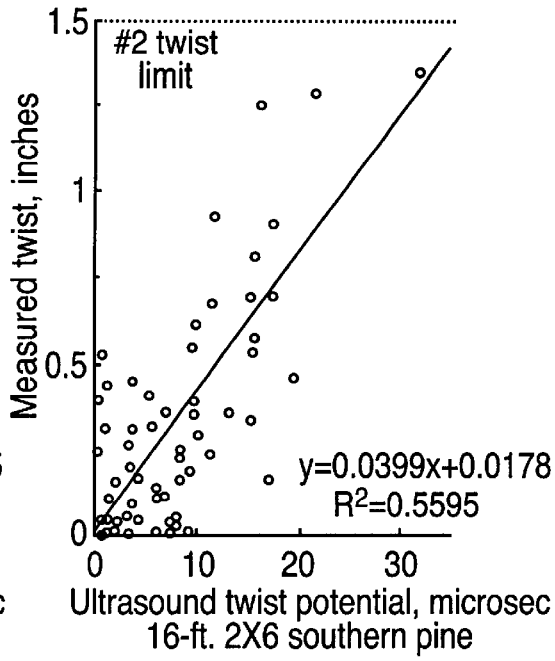
Figure 4C:
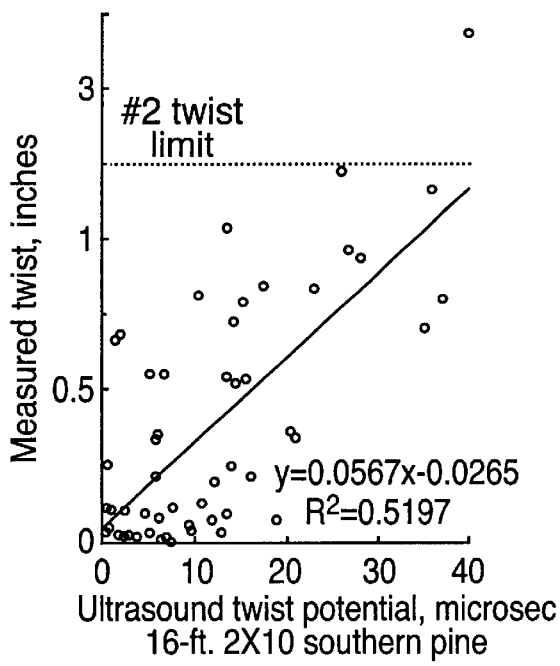
Figure 4D:
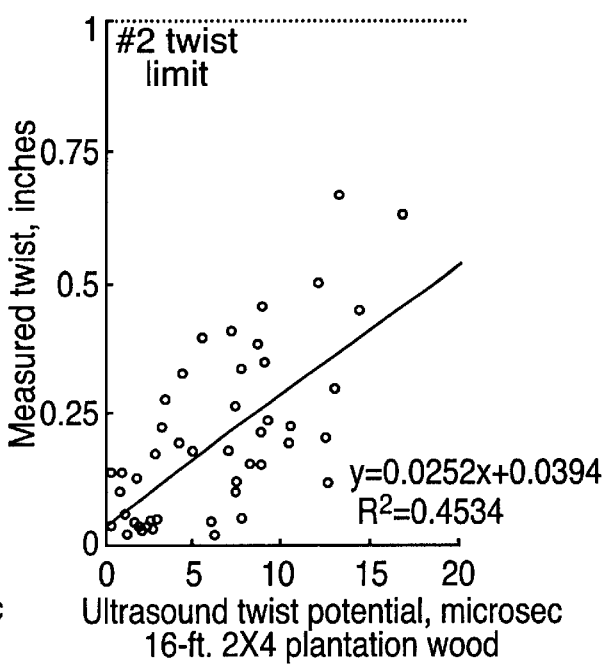

Particular embodiments of the present invention determined grain angles using acoustic energy, electromagnetic energy, electrical energy and combinations thereof. Working embodiments have, for example, used laser scanning methods, including the apparatus of U.S. Pat. No. 4,606,645 (which is incorporated herein by reference), to determine grain dive angles based on patterns of reflection of laser light off the surface of wood. The use of laser-scanning devices is illustrated by FIG. 1. In a working embodiment, laser grain angle measurements were gathered at three locations across the board (at the edges and in the middle of the board) every 7 inches along the length of a board. The laser scanner provided both in plane surface and out-of-plane surface (dive) angle readings. In this working embodiment, as illustrated in FIG. 2, grain angles were measured in patches of 9 readings arranged in a 3-by-3 matrix with the intent to capture and smooth the localized variation in grain angle.

Other embodiments of the present invention measure spiral grain (a type of grain angle) of trees or logs by analyzing patterns of bark or cambium. Spiral grain of trees or logs also can be measured by cutting a planar surface through the bark and cambium into the wood of a tree or log and measuring the dive angle patterns by laser scanner.

Additionally, the method of the present invention can be practiced by observing the spiral grain patterns on the exterior surface of a log or tree. The grain angle patterns within the interior of a log or tree also can be estimated using acoustic velocities around the perimeter of the log or tree. A log or tree where these perimeter measurements indicate the presence of spiral grain will likely contain more twist prone wood than a log or tree where these measurements reveal no spiral grain.

Still other working embodiments use electricity to determine grain angles. For example, working embodiments measure dielectric potentials of wood to determine one or more grain angles. Such embodiments used the commercially available Metriguard™ Model 520 Grain Angle Indicator, which is available from Metriguard, Inc. of Pullman, Wash., or other similar devices.

FIG. 3 demonstrates that grain angle measurements can be accurately determined using a variety of methods. This figure is based on data collected by scanning 1×6 inch boards cut from 24 year-old Loblolly pine. Laser scanning was accomplished by the method of U.S. Pat. No. 4,606,645. Microscopic measurements were taken by light microscope observation of the wood surface. Dielectric measurements were taken using the Metriguard apparatus.

Other working embodiments use acoustic energy, particularly ultrasound energy, to determine grain angles. Ultrasound is understood to mean sound frequencies of about ten kilohertz to about several megahertz. For continuity, all ultrasound measurements discussed herein were performed with the testing device at a single frequency, which was 14 kHz. However, different ultrasound frequencies or plural ultrasound frequencies can be used with the method of the present invention.

Working embodiments measured the velocities of ultrasound pulses through wood to determine one or more grain angles. Such embodiments used the commercially available Sylvatest® apparatus, which is available from-Sandes SA, Granges/Veveyse, Switzerland.

The use of acoustic energy is not limited to such devices, however. A person of ordinary skill in the art will realize that other sounding or resonating devices, or other frequencies may be utilized, so long as the acoustic signal may properly propagate through the wood. In fact, any device which causes an acoustic signal to propagate through the wood may be used in the present invention, including the acoustic signals generated in wood by a saw, planer, or sander during the milling process.

2. Nondestructive Measurements of Grain Angle

Previous methods for measuring grain angle (see, e.g., Brazier) were destructive, whereas working embodiments of the present invention provide nondestructive methods for determining crook and/or twist potential in lumber.

3. Ultrasound

Working embodiments of the invention provide nondestructive methods for measuring grain angle. In particular, ultrasound propagation measurements are used to determine the twist potential for a piece of wood. For example, FIG. 4 illustrates the twist potential determined using ultrasound versus the actual measured twist for 16-foot boards cut from different types of wood (hemlock, southern pine, and plantationwood) in different cross-sectional sizes. In each case, twist potential was determined by averaging the differences in the cross-diagonal ultrasound time differential (see, e.g., FIG. 13) measurements taken at each edge of the board at the positions indicated along the length of the board. As shown, the determined twist potentials accurately correlate to the actual measured twists with $R^2$ values of about 0.50.

When using ultrasound to measure grain angle, the effect of knots and other defects (which can alter the ultrasound velocity or path and can therefore affect the unit time measurement) should be addressed. Localized defects, such as knots, generally have local impacts on the ultrasound signal. For example, one particular 2×6 specimen (#5256) had knotty regions near the 4-ft. and 8-ft. locations, which coincide closely with anomalous spikes in the ultrasound profiles. Such "noise" can interfere with identification of edge-to-edge grain angle variations. Thus, working embodiments of the present method that used ultrasound to measure grain angle compensated for the noise to better distinguish twist-prone lumber. One way to compensate for such noise is simply to ignore measurements with these anomalies. Another way to compensate for such noise would be to use statistical algorithms, which reduce the significance of anonomolous measurements.

A related issue concerns the span along the length of the board over which the diagonal unit times are measured. For longer spans, or for thinner boards, the cross-diagonal paths become closer to parallel and consequently, the difference in the two unit times is reduced for any given grain angle. Therefore, for a given board thickness, the maximum feasible span is a function of the need to maintain significant unit time differences. A comparison of determined twist potentials using both 12-inch and 24-inch spans showed that either span could be used to distinguish twist-prone pieces, at least for material that was two inches thick.

4. Measuring locations

Grain angles can be measured at particular measuring locations along the wood. A measuring location is understood to be a location on or within the wood where a grain angle is measured. For example, working embodiments of the invention have measured grain angles according to ultrasound velocity. Ultrasound velocity was measured by the elapsed travel time of an ultrasound pulse through wood from a first transducer to a second transducer. In such an embodiment, a measuring location would be the segment of wood located substantially around and between the transducers.

Measuring locations may be separated by at least one predetermined distance based on factors such as the spatial dimensions of the wood being studied, type of wood, and methods used to measure grain angles. Some working embodiments employ measuring locations spaced along one or both edges of a board by a predetermined distance of from about 12 to about 48 inches. Alternative embodiments use a predetermined distance of about a foot for separating measuring locations along the lengthwise span of the board.

Not every measuring location needs to be separated by the same predetermined distance, and predetermined distances may vary along the axes of the wood (see, e.g., FIG. 1). For example, measuring locations might be spaced every foot along the length of the wood while spaced by less than an inch across the width or face of the wood. In some embodiments, measuring locations may touch or even overlap (see, e.g., FIG. 2 where each dark circle represents a measuring location). Also a first pair of measuring locations may be separated by a first distance that is the same as, substantially the same as, longer or shorter than a second distance between a second pair of measuring locations.

Figure 5:
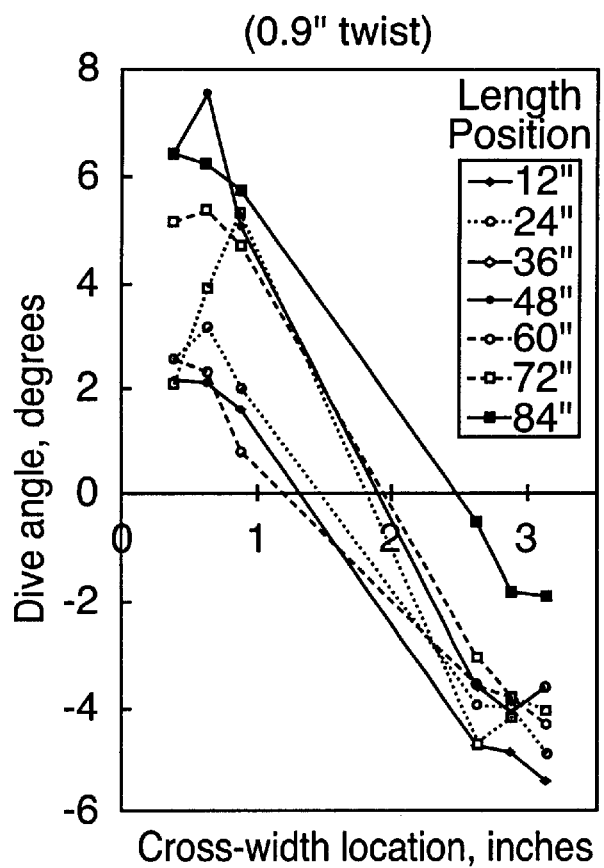
FIG. 5 illustrates a dive angle profile for a twisted piece of wood.

For example, FIG. 5 shows an 8-foot long, 2-by-four inch SPF board with measuring locations clustered at the edges of the board at one-foot intervals down the length of the board.

5. Grain Angle Measurements Obtained from Third Parties

Grain angles may be measured by the person, or persons, practicing the invention (as described above). Grain angle measurements also may be obtained from a third party. For example, the user of the invention could be a computer technician who does not specifically measure grain angles in a piece of wood, but instead analyzes a collection of grain angles supplied by a third party.

D. Determining Twist Potential

Once the at least one grain angle is obtained, the twist potential for the wood can be determined. The method of the present invention can employ one grain angle or plural grain angles to determine twist potential. If plural grain angles are measured, the pattern of grain angles may be analyzed.

The twist potential of wood depends on the pattern of grain angle within the piece. As currently understood, twist potential appears to be related to the edge-to-edge grain angle variation within the board (here grain angle refers to the dive angle as viewed from the face of the board), such as the grain angle patterns illustrated in FIGS. 5, 7 and 11B. In contrast, straight boards (i.e. boards with substantially little or no twist) exhibit little or substantially no such edge-to-edge variation in grain angle, such as the grain angle pattern illustrated in FIGS. 6 and 11A.

Figure 6:
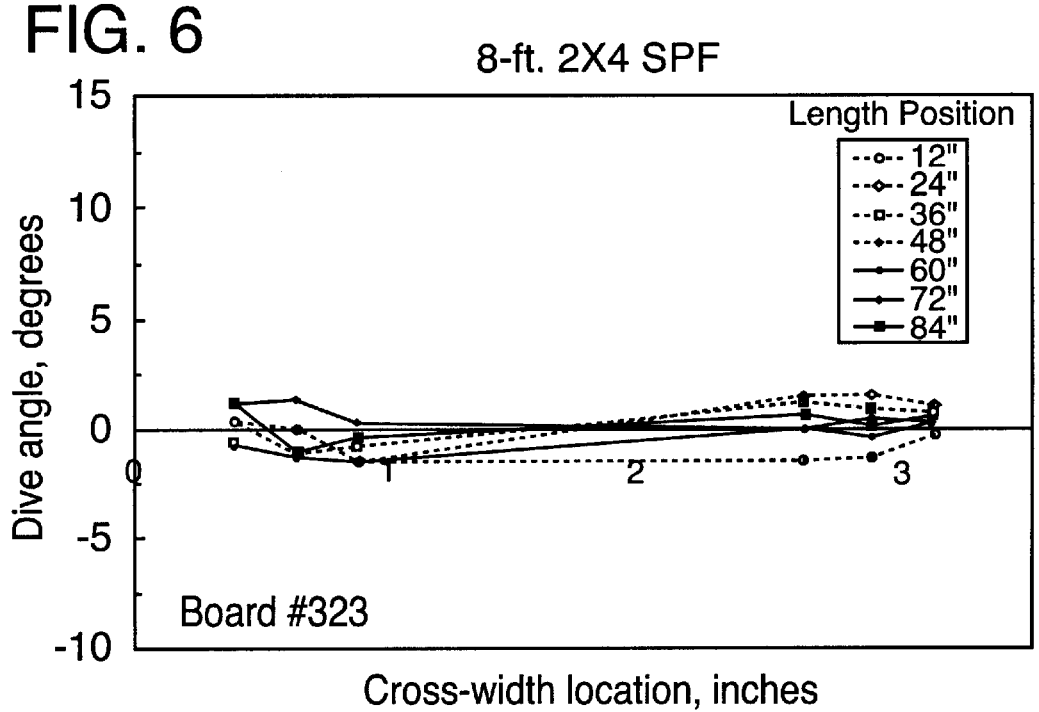
FIG. 6 illustrates a dive angle profile for a straight piece of wood.

In FIGS. 5–7, dive angles were measured by the laser-scattering method of U.S. Pat. No. 4,606,645. In FIGS. 8–10, grain angles were determined using the same ultrasonic technique illustrated in FIGS. 12–13. The SPF studs were purchased on the commercial market. Other boards were cut from 15 year-old loblolly pine and mill-run hemlock.

The relationship between edge-to-edge grain angle variation and determining twist potential can easily be seen by comparing FIG. 6 with FIG. 7. In FIG. 7, dive angles consistently vary across the width of the board. For example, at length position 60 inches, grain angle at the lowest cross-width location (approximately 0.4 inches) is approximately 3 degrees in the positive direction, while the grain angle at the same length position at the highest cross-width location (approximately 3.1 inches) is approximately 3 degrees in the negative direction. In contrast, the dive angles of FIG. 6 vary only slightly across the width of the board and are consistently less than 2.5 degrees in magnitude. This difference in edge-to-edge grain angle variation in twisted versus straight boards is further illustrated by comparing FIGS. 5, 8A–C, 9A–B, 10A–B and 11A–C.

Lumber with a potential to twist therefore is identifiable by a consistently lower grain (dive) angle (as viewed from the board's face, or wider surface) at or near one edge of the piece, and a higher grain (dive) angle at or near the opposite edge.

Not only can twist-prone pieces of wood be identified from determined twist potentials, but particular twist-prone regions can be identified within a piece of wood when determining twist potential for the wood.

1. Edge-to-Edge Variation in Grain Angles Measured by Ultrasound

Working embodiments typically have used plural grain angles for detecting edge-to-edge variation in grain angles across the face of a board. Sample results from such embodiments are shown in FIGS. 8–10 for a variety of board dimensions and materials. Each graph of FIGS. 8–10 illustrates the difference between cross-diagonal ultrasound unit time measurements taken along one edge of a board with the difference observed along the other edge. Since the difference between cross-diagonal ultrasound unit times can be correlated to grain angle, edge-to-edge variation in the difference between cross-diagonal ultrasound unit times indicates a similar edge-to-edge variation in grain angle. Ultrasound scans of a number of twisted and straight boards of varied dimensions and from different raw material sources confirmed the feasibility of distinguishing twist-prone lumber from stable lumber and serve to illustrate the method.

Figure 8A:
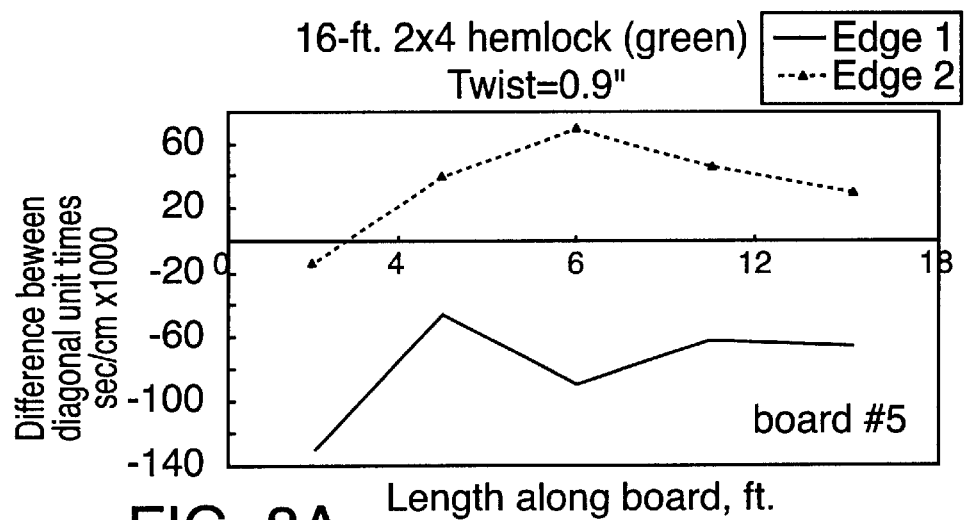
FIG. 8 illustrates typical ultrasound profiles for twisted and straight 2×4 inch boards.
Figure 8B:
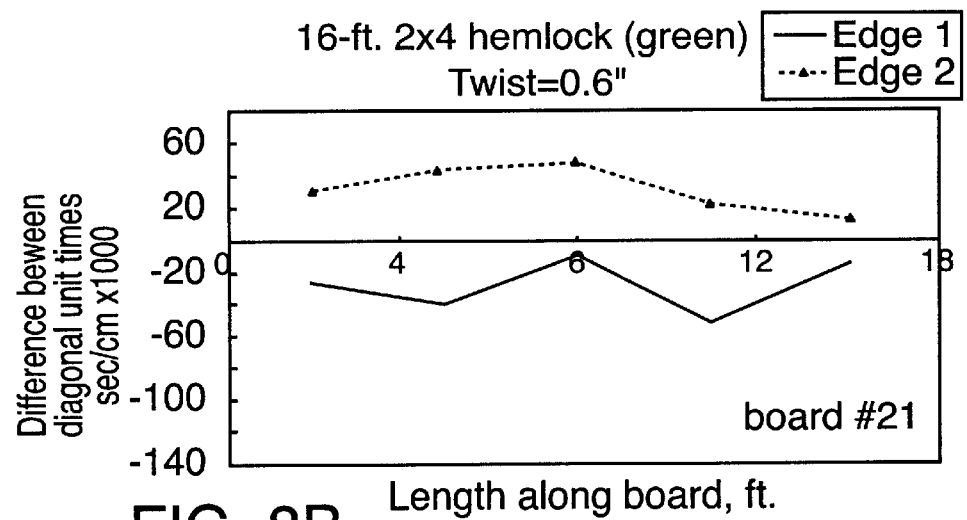
Figure 9A:
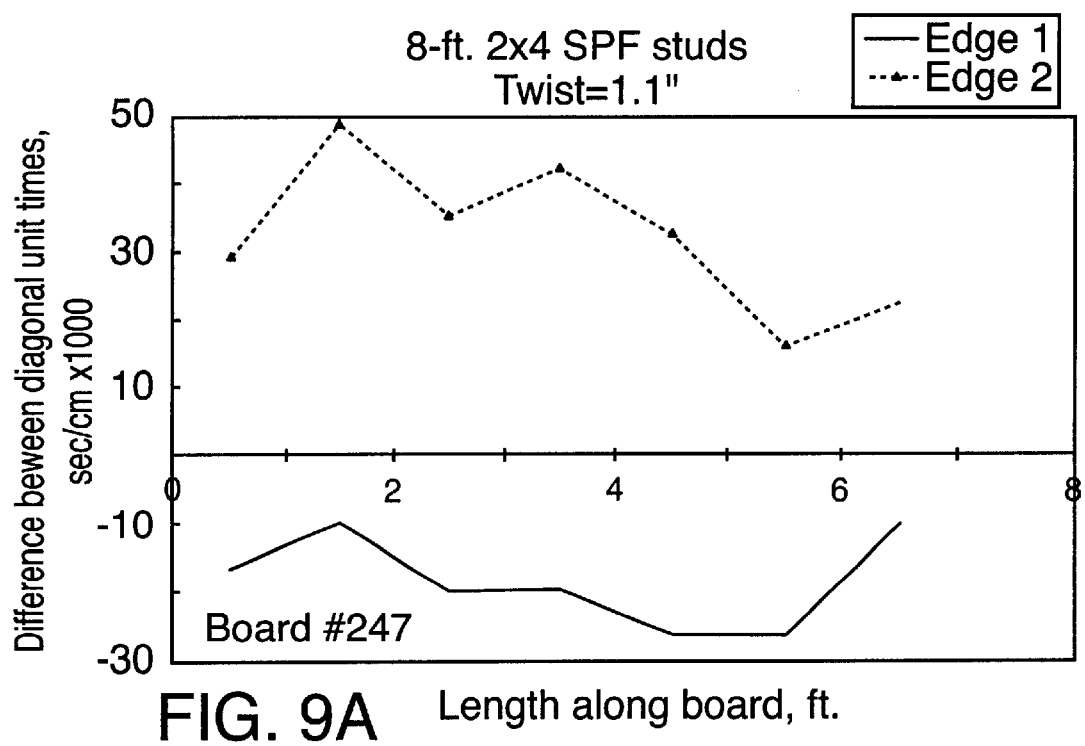
FIG. 9 illustrates typical ultrasound profiles for a twisted and a straight 2×4 inch board.
Figure 10A:
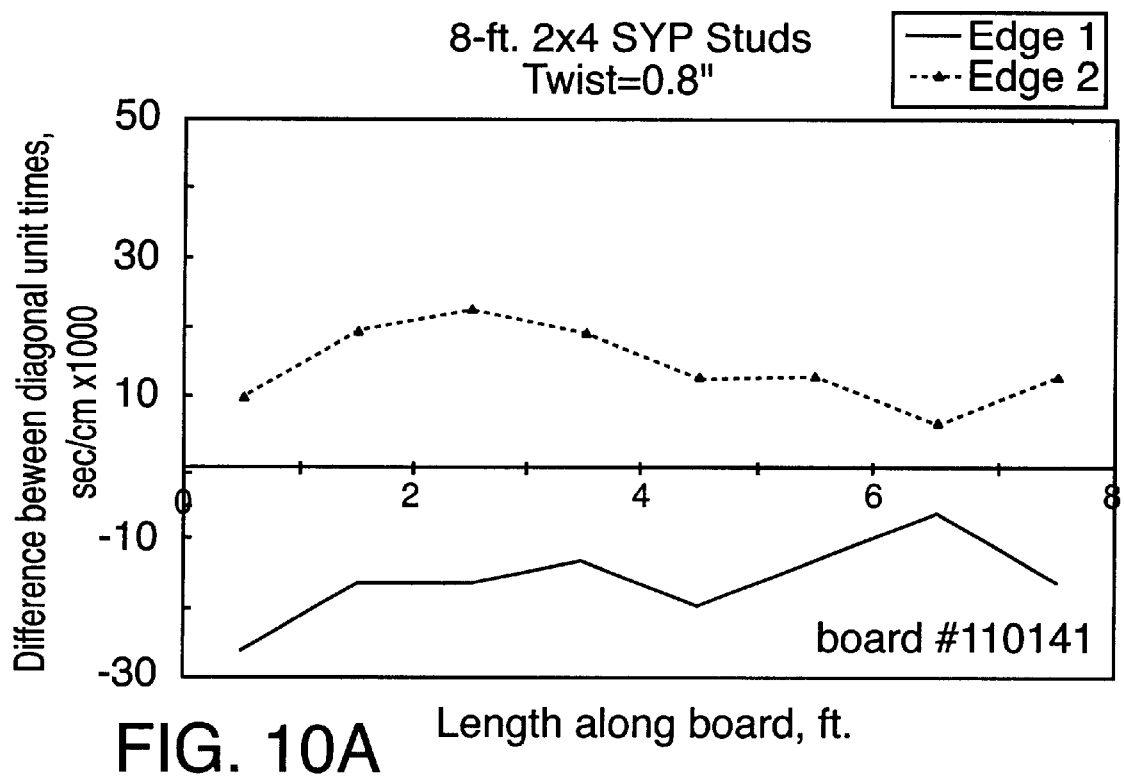
FIG. 10 illustrates typical ultrasound profiles for a twisted and a straight 2×4 inch board.

In twist-prone pieces (i.e. where twist potential was determined to be higher than in straight pieces), the pattern of grain angles along one edge is dissimilar to the pattern of grain angles along the other edge. In particular, in twist-prone pieces, the grain (dive) angles (as measured by ultrasound) along one edge are consistently higher or lower (in magnitude, direction or both) than the grain (dive) angles along the other edge. For example, FIG. 8A shows such variation in grain angles. The board of FIG. 8A (board #5) was a 16-foot long two-by-four cut from hemlock. These ultrasound measurements were plotted as differences between diagonal unit times as an indicator of grain angle (see Example #2 below). Similar edge-to-edge variations in ultrasound measurements also are seen in FIGS. 8B, 9A and 10A.

Figure 8C:
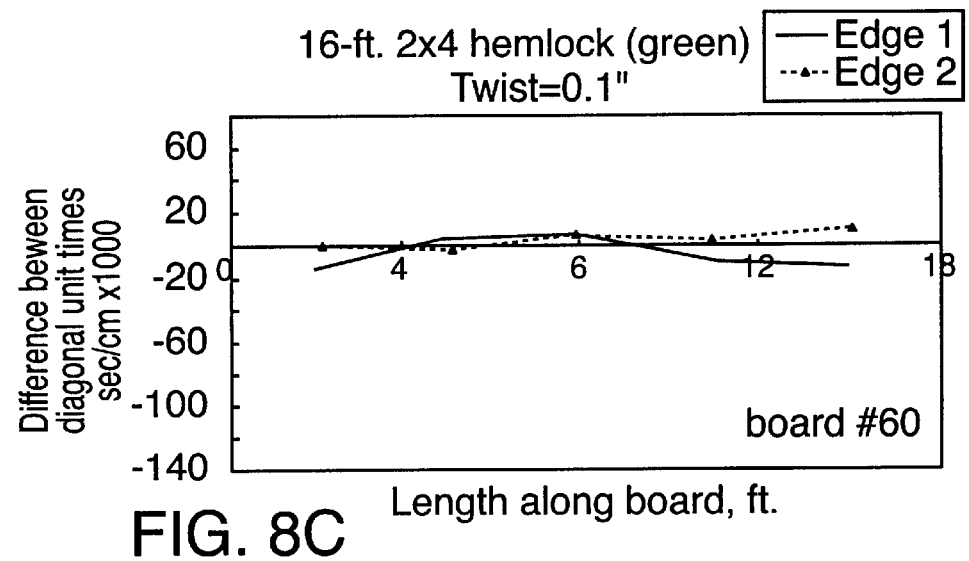
Figure 9B:
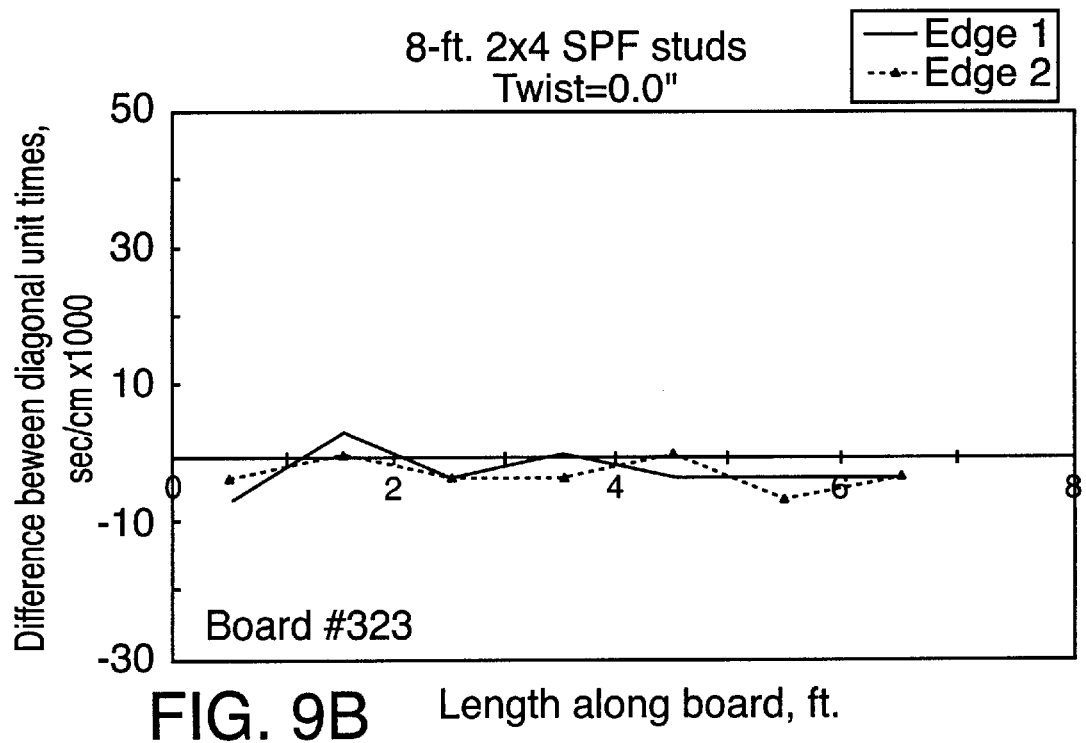
Figure 10B:
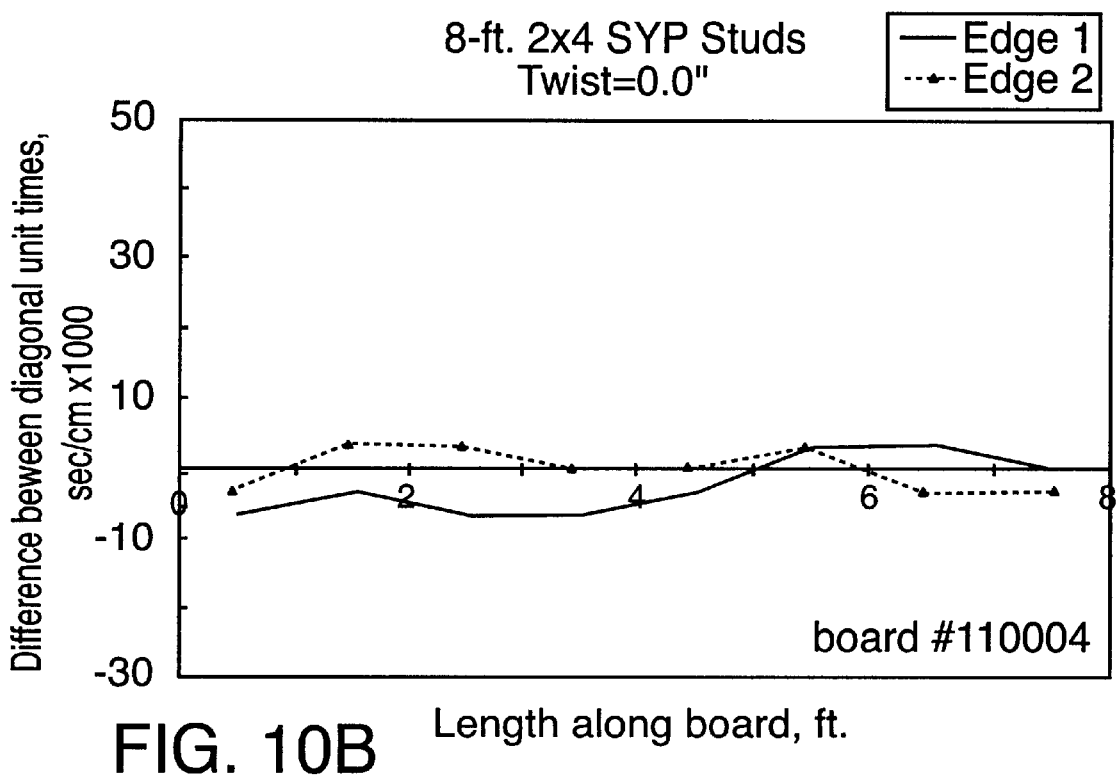

In straight, stable lumber, the pattern of grain angles along one edge is similar to that along the other edge in terms of grain angle magnitude and direction. For example, the board illustrated in FIG. 8C shows such a similar relationship. The board of FIG. 8C was a 16-foot long two-by-four cut from hemlock. Ultrasound measurements were taken along each edge and plotted as differences between diagonal unit times as an indicator of grain angle (see Example #2 below). Similar edge-to-edge consistency in ultrasound measurements is also seen in FIGS. 9B and 10B as well.

2. Edge-to-Edge Variation in Grain Angles Measured by Laser Scattering

Figures 11A, 11B, 11C:
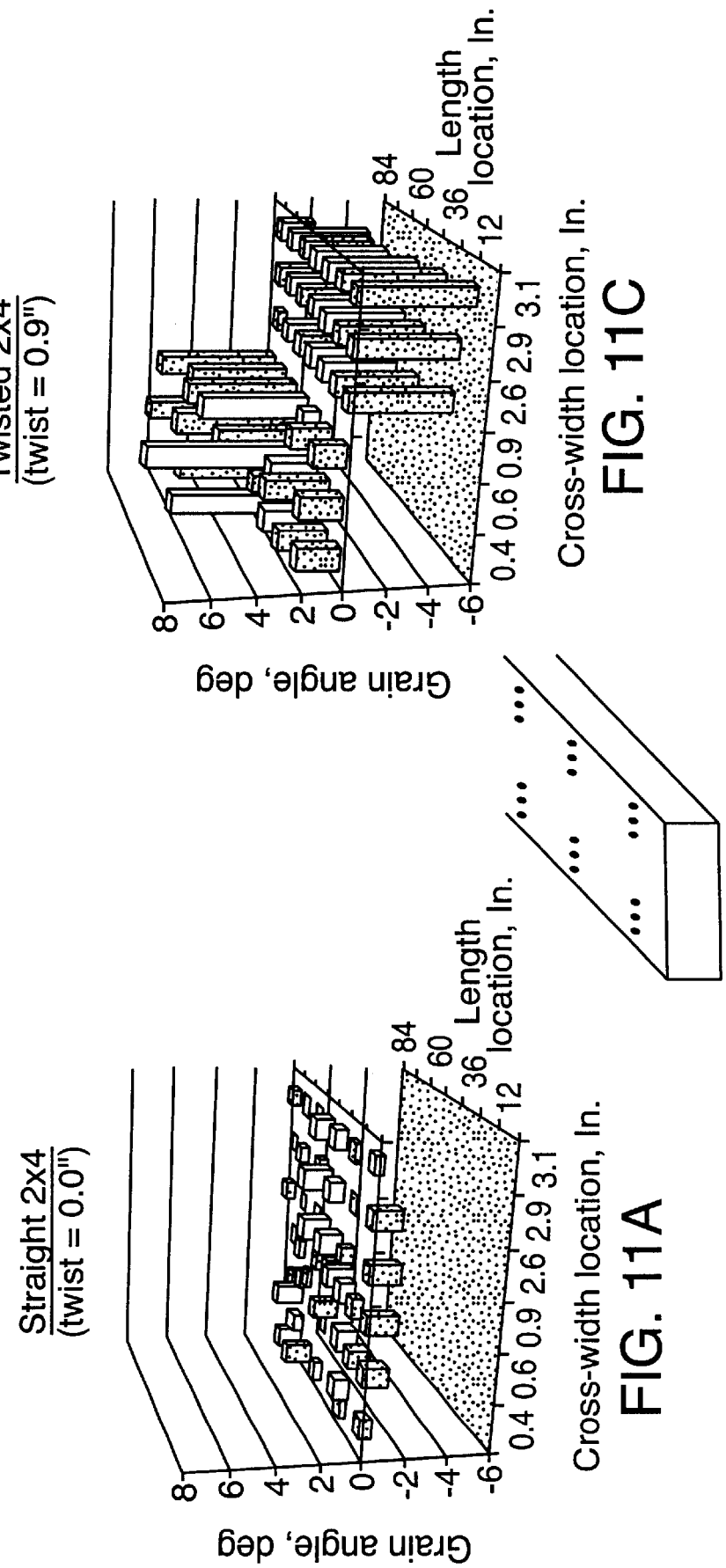
FIG. 11 illustrates grain angle maps for a twisted and a straight 2×4 inch board.

FIG. 11 shows that edge-to-edge variation in grain angles also can be measured and detected by laser scattering. Here, grain angles were determined by dive angle measurements taken at locations substantially adjacent to the edges of a board. In particular, dive angle measurements were taken on eight-foot long SPF two-by-fours obtained from the commercial market. Dive angles were plotted two-dimensionally. FIG. 11A shows the pattern of dive angles in the straight board. Dive angles were generally less than 2 degrees in magnitude and no consistent edge-to-edge variations existed. FIG. 11B shows the pattern of dive angles in the twisted board. Dive angles were generally greater than 2 degrees in magnitude and, at each interval down the length of the board, a consistent edge-to-edge trend in dive angles was seen. For example, at the 12-inch length location, dive angles at the proximate cross-width locations (0.4 to 0.9 inches) were about 2 degrees in the positive direction while dive angles at the distant cross-width locations (2.6 to 3.1 inches) were 4 to 6 degrees in the negative direction.

E. After Determination of Twist Potential

If sufficiently accurate measurements are obtained, the resulting information enables trim decisions to be made based on twist potential. That is, trimming may be utilized to eliminate highly unstable twisted ends, if such twisting is severe enough to cause the entire length to be downgraded. Other processing techniques (such as kiln-drying under restraint) may be used.

Subsequently, actual twist can be measured after drying and compared to the predicted twist based on the determined twist potential. The accuracy of the model used to determine twist potential can then be refined or extrapolated to other similar pieces.

F. Silviculture

Twist potential can also be used in silvicultural practices and manufacturing processes. For example, harvesting decisions for particular stands of trees could be made in the field. Trees having high twist potential could be thinned from a stand and directed to applications where the twist potential of the harvested wood is not an important consideration (e.g. chipping, use as lumber for pallets, etc.). Under such a practice, the overall quality of wood in the entire stand would improve. Alternatively, trees having low twist potentials could be harvested as a source of wood for structural applications.

Raw logs could be analyzed in the field and distributed to appropriate destinations. For example, logs having high twist potentials could be sent to paper mills for processing while logs having low twist potentials could be sent to lumber mills for manufacturing into planks, boards, studs and other types of lumber.

Particular pieces of lumber could be analyzed for use in particularly sensitive applications. For example, boards having very low twist potentials could be designated for further processing and manufacture into products used in environments where humidity or equilibrium moisture contents vary considerably.

Additionally, the method of the present invention could be practiced using determined twist potential thresholds. A first threshold may be set (e.g. an average across-the-board differential in the difference in diagonal unit times of 0.050 sec/km) with boards meeting or exceeding this threshold being separated out for specific handling and/or uses where twisting is not a significant concern. Also, boards with a twist angle variation at a second higher level could be further separated for different handling. Any number of thresholds could be set.

G. DIMENS Model

A three-dimensional finite element model (FEM) for wood, called DIMENS, was developed which successfully and accurately determines warp potential-including twist potential-given measurements of wood characteristics such as grain angles. The DIMENS model describes the strains that arise in a piece of wood during a change in moisture content. In the DIMENS model, local strains were initially determined by a number of localized physical parameters, including moisture-related shrinkage coefficients, normal and shear moduli of elasticity, and fiber grain angles. The DIMENS model provides a tool for studying the influence of factors affecting dimensional stability of wood and to determine twist potential. While using DIMENS is not necessary in determining twist potential, the use of DIMENS would improve the accuracy of determining twist potential.

One of ordinary skill in the art will appreciate that DIMENS provides only one basis for practicing the present invention. Alternative FEM's for determining twist potential, if used, could be developed using methods of the present invention.

Figure 16:
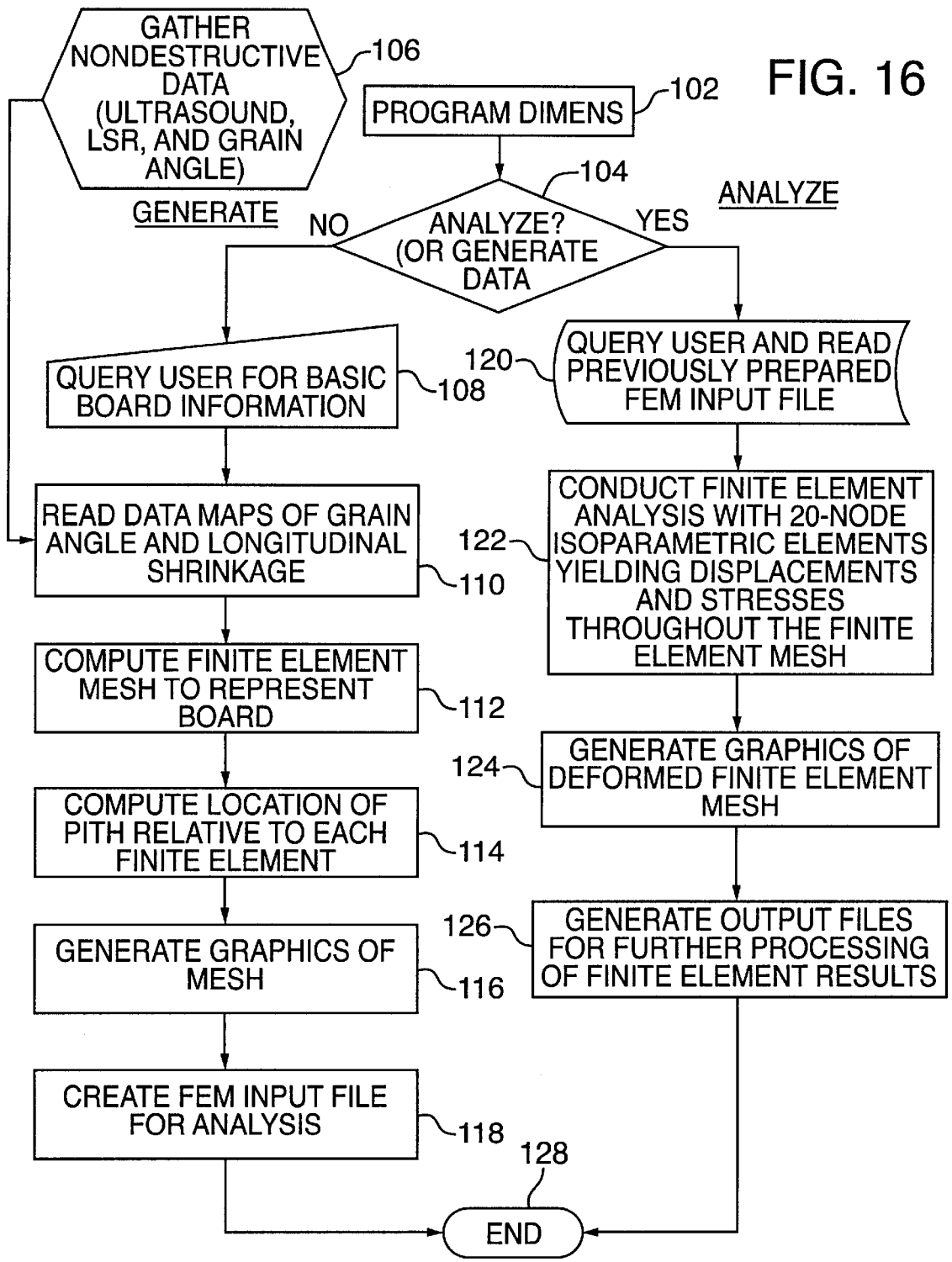
FIG. 16 is a functional flowchart illustrating the DIMENS computer model.

One embodiment of the DIMENS model is illustrated by the functional flow-chart of FIG. 16. Another embodiment is provided by the computer program source code listed in Appendix A.

H. EXAMPLES

The following examples concerning twist are provided to illustrate particular features of the present invention. The scope of the present invention should not be limited to those features exemplified.

Example #1

Laser-Scattering Detection of Grain Angle

FIGS. 5–7 illustrate the typical pattern of grain angle in twisted boards as compared to that in straight pieces. Twist was measured as the moisture content of the boards was altered by reducing the relative humidity (RH) from 90% RH to 20% RH (causing a change in the wood's equilibrium moisture content from about 20% db to about 5% db). Grain angles were measured on eight-foot long SPF boards measuring two inches high by four inches wide. Fiber angles were measured on the face of the boards at one-foot intervals using a laser scattering method (see U.S. Pat. No. 4,606,645) which provides both the dive and surface angle components of the fiber angle. FIG. 11C illustrates the grid pattern used to make grain angle measurements.

Lumber that is prone to twist typically exhibited a recognizable trend of increasing or decreasing fiber dive angle from one edge to the other edge across the face of the board. Boards that did not twist exhibited little or no such consistent trend. In many twisted pieces, the sign of the dive angle changed from one edge of the board to the opposite edge (see, e.g., FIG. 5).

Example #2

Ultrasound Detection of Grain Angle

Figure 12:
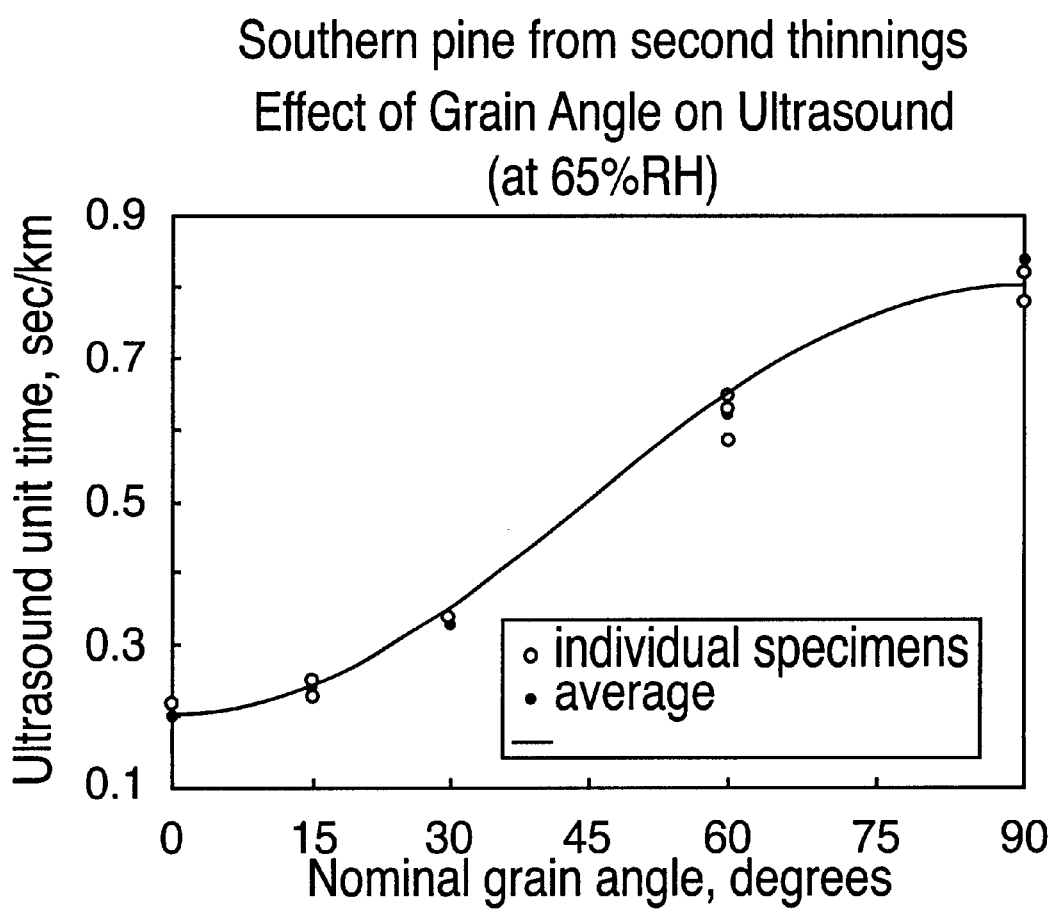
FIG. 12 illustrates effects of grain angle on ultrasound unit time and swelling rate.

In testing for crook-prone lumber, ultrasound tests were conducted on wood samples to determine ultrasound velocity, shrinkage, and grain angle within the wood samples. FIG. 12 illustrates that ultrasound unit time (inverse velocity measured in sec/km) increases with increasing grain angle. This relationship makes it possible to use ultrasound to detect variations in grain angle.

Figure 13A:
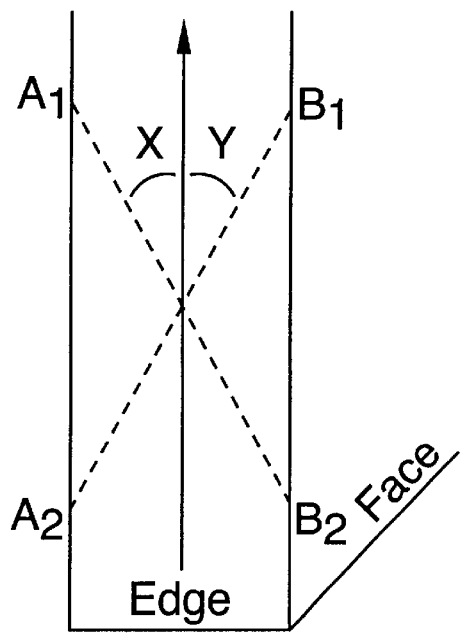
FIG. 13 illustrates using ultrasound to detect grain angle differences.
Figure 13B:
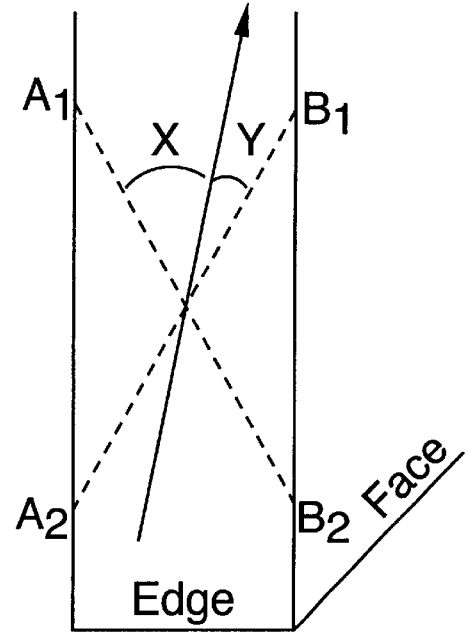

One way to detect grain angle differences, in particular, is illustrated in FIG. 13. In this method, the ultrasound unit time of travel was measured on a first path ($A_1$–$B_2$) through the board from one face to the other face, and also along a second path ($A_2$–$B_1$) through the board from one face to the other face. If the dive angle is zero (FIG. 13A), the angles X and Y are identical. Therefore, the ultrasound unit times (inverse velocities) along these paths are identical. If the dive angle is not zero (FIG. 13B), the angles X and Y are different, and the ultrasound unit times along the two cross-diagonal paths are different. The relative values of these two ultrasound unit times will indicate the sign of the grain angle, and the difference between them will relate to the magnitude of the grain angle.

Figure 14:
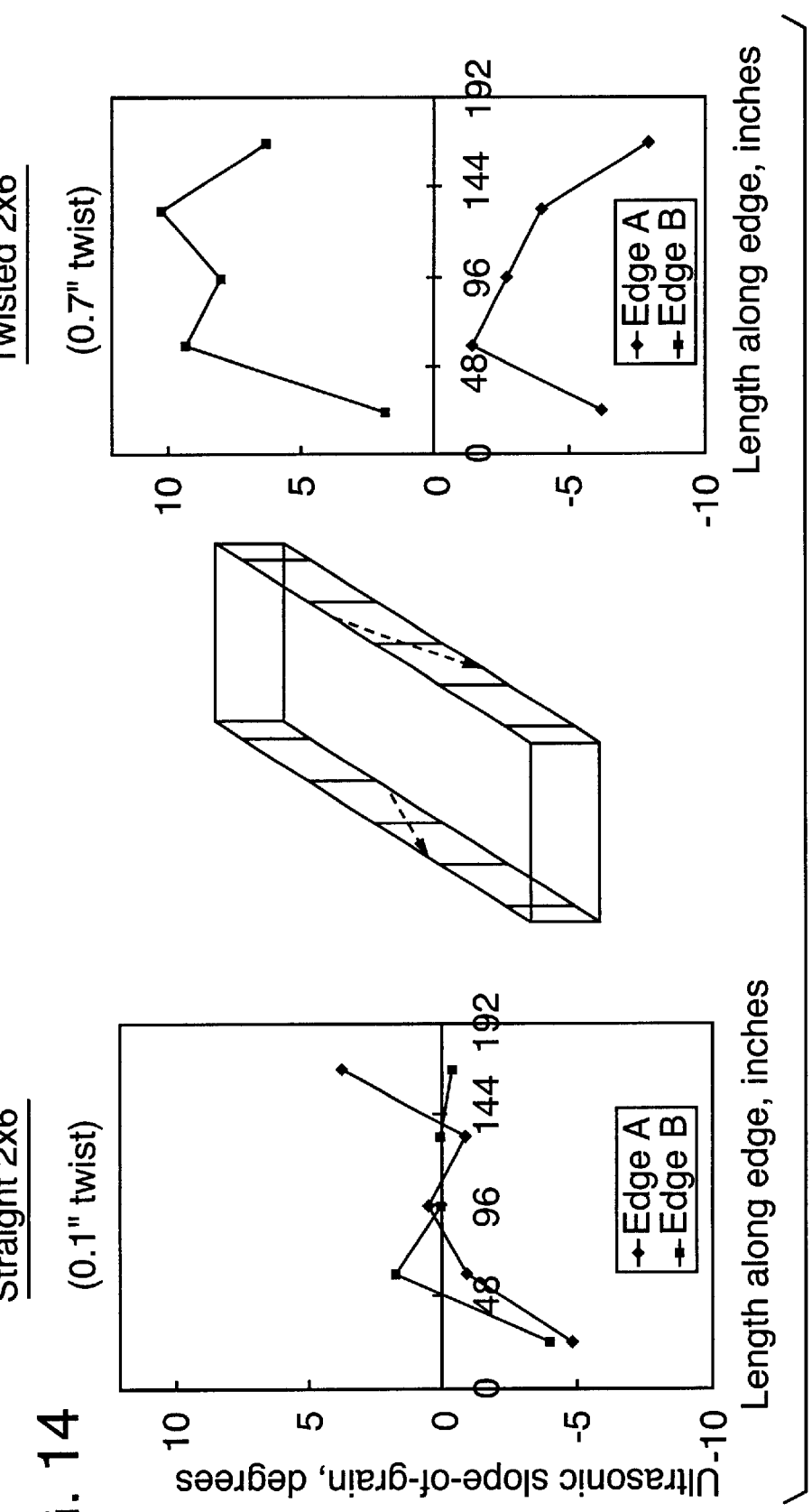
FIG. 14 illustrates typical ultrasound profiles for straight and twisted 2×6 inch boards.

Consequently, twist potential for lumber will be indicated in general by differences in ultrasound unit times taken at one or more measuring locations on the lumber. Additionally, a person practicing the present invention could detect a consistent trend of increasing or decreasing difference in ultrasound unit times along the first and second paths taken at measuring locations spread across the face of a board from edge to edge (see, e.g., FIGS. 8–10). In many cases, this consistent trend appears as a change in direction of grain angles from the positive direction at one edge of the board to the negative direction at the other edge of the board, as shown in FIG. 14.

Example #3

Green Lumber

A number of the examples discussed above have used ultrasound measurements from kiln-dried lumber samples. To predict the twist potential in lumber prior to drying, working embodiments must necessarily rely on ultrasound measurements of green lumber. Results were obtained by applying a Sylvatest® ultrasound test to sixty-one 16-ft. lengths of green 2×4 hemlock. The lumber was then kiln-dried and planed. Finally, the moisture content, crook, bow, and twist of each piece were measured.

This test confirmed that the same relation between twist potential and the edge-to-edge differential in the diagonal unit time difference found in dry pieces exists in green lumber. Therefore, tests in green wood will predict warp defects in processed wood.

Figure 15:
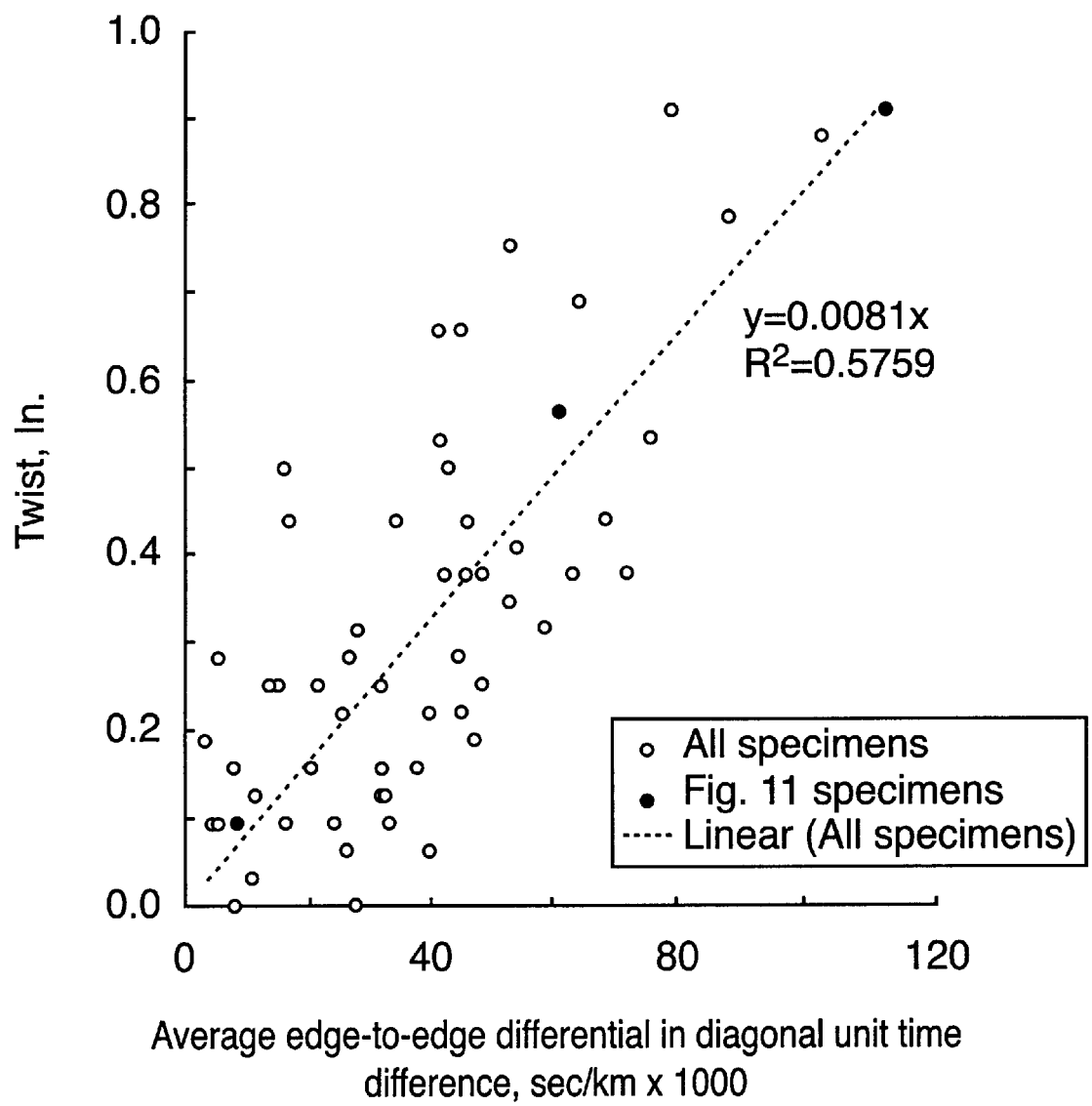
FIG. 15 illustrates correlation between twist and ultrasound measurements.

To compare the results from all 61 boards, an average edge-to-edge differential was calculated for each board by averaging the differentials at the five measuring locations along each length. FIG. 15 shows how the measured dry twist relates to the averaged green ultrasound data. An obvious correlation appears, with a linear $R^2$ of about 0.58. Although moderate scatter exists, even these simple average differentials are selective enough to serve as a useful predictor of twist potential in green lumber.

Having illustrated and described the principles of our invention with reference to several specific examples, it should be apparent that these examples may be varied in arrangement and detail without departing from these principles.

APPENDIX A

```
      PROGRAM DIMENS

5    USE MSFLIB

C    PROGRAM TO CREATE A SIMPLE RECTANGULAR MESH AND
           DISPLAY IT

10    C    LINEAR ELASTIC FNIITE ELEMENT ANALYSIS WITH INITIAL
           STRAINS

C    WRITTEN BY STEVEN CRAMER - UNIVERSITY OF WISCONSIN -
           1997
15
      C    WITH CONTRIBUTIONS FROM W. CHEN - 1986 AND OTHERS -
           1997

C    IMPLICIT DOUBLE PRECISION (A-H,O-Z), INTEGER(I-N)
20
      CHARACTER*3 ANSWER

CHARACTER*1 AXIS

25    CHARACTER*70 WTITLE,FNAME

INTEGER*2  IHR,IDAY,IMIN,IMON,IYR,ISEC,I100TH

LOGICAL ANALY,SHONODNO
30
      COMMON/KONTRL/NUMNOD,NDOF,NELE,NNPE,NSD,NEQ,IBAND

COMMON/LIMITS/MAXELE,MAXNOD

35    COMMON/CPDS/CORD(3,5000),FEXT(15000),disp(15000)

COMMON/BOARD/BODIMY,BODIMX,BODIMZ,YINC,XINC,ZINC,NELX,NELY,
      NELZ

40    COMMON/ELEM/KFIX(3,5000),LINK(20,2500),MAT(2500)

COMMON /MATRL / NMAT,RMAT(9,2500)

COMMON /DEVICE/ IIN,IOUT,IBUG,NGP,IWP,ITP,INP,IEP
45
      COMMON/VIEW/AXIS,WTITLE,VIEWD,SHONODNO,ANALY,SMAG
      COMMON/INTR/IHR,IDAY,IMIN,IMON,IYR,ISEC,I100TH
      ANALY=.FALSE.

50    SMAG=0.0
```

```
         C

C     CONTROL SIZE OF WINDOW

5       CALL WSIZER              !open file 10 as terminal window

C

C     SET PROGRAM LIMITS
10       C

MAXNOD=5000

15       MAXELE=2500

C

C     SET PROGRAM CONTROL VALUES
20       C

NDOF=3

25       NNPE=20

NSD=3

NGP=27
30       ITP=0

INP=1

35       IEP=1

C

C     BRANCH BETWEEN ANALYSIS AND PROBLEM SETUP MODE
40       C

WRITE(10,2000)
         READ(10,*) ANSWER
45
         C     ANALYSIS MODE

C***********************************************************
         IF(ANSWER.EQ.'YES'.OR.ANSWER.EQ.'yes') THEN
50       WRITE(10,2030)
         WRITE(10,2010)
```

```
        READ(10,*) FNAME
        IIN=5
        IOUT=16
        Do 7 I = 1,9
 5      If (Fname(I:I) .EQ. '.')Goto 8
        7 Continue
        8 I = I-1
        OPEN(5,FILE=Fname(:I) // '.dat')    ! 5 & ?.dat = INPUT
        OPEN(16,FILE=Fname(:I) // '.out')   ! 16 & ?.out = OUTPUT
10      OPEN(11,FILE=Fname(:I) // '.ang')   ! 11 & ?.ang = angles for plotting
        OPEN(12,FILE=Fname(:I) // '.plt')   ! 12 & ?.plt = FOR PLOTTING
        OPEN(13,FILE=Fname(:I) // '.crk')   ! 13 & ?.crk = displacements FOR
        PLOTTING
        CALL READIN
15      C
        C       INITIALIZE DISPLACEMENT ARRAY
        C
        NEQ=NUMNOD*NDOF
        DO 10 J=1,NEQ
20      DISP(J)=0.0
        10              CONTINUE
        C
        CALL GETTIM(ihr,imin,isec,i100th)
        CALL ANALYZE
25      CALL PLOTOUT
        CALL TIMIT
        ANALY=.TRUE.
        CALL DRAWSECT
        C       going to need to work with planes
30      c               three-D point plot is not visible in AXUM
        C
        C       OPEN TEXT/DATA FILES
        C
        C       OPEN (5,FILE='ORTHO3D1.DAT')
35      C       OPEN(5,FILE='TRYIN2.DAT')
        c       OPEN (6,FILE='ANGLES.DAT')
        C    OPEN (16,FILE='DIMENS.OUT')
        ELSE
        C
40      C       PROBLEM SETUP - MESH GENERATION AND PROPERTY ASSIGNMENT
        C*************************************************************
        WRITE(10,2010)
        READ(10,*) FNAME
        WRITE(10,2020)
45      Do 17 I = 1,9
        If (Fname(I:I) .EQ. '.')Goto 18
        17              Continue
        18              I = I-1
        IOUT=16
50      OPEN(16,FILE=Fname(:I) // '.dat') !16 & ?.dat = output
        OPEN(14,FILE=Fname(:I) // '.gaa')   OPEN(15,FILE=Fname(:I) // '.gab')
```

DPP:SDY:JOC:ejk:dm 9/2/99 1574-53412 Ref. No. 22886   EXPRESS MAIL LABEL NO. EL121365070US
                                                      Date of Deposit: September 2, 1999
-23-

```
       OPEN(13,FILE=Fname(:I) // '.lse')
       C           13 & ?.lse = measured shrinkage and E data
       C           SEE SUBROUTINE SHRNKEIN FOR MORE INFO ON FILE 13
       C           14 & ?.gaa = grain angle data on A Face
  5    C           15 & ?.gab = grain angle data on B Face
       C           SEE SUBROUTINE ANGLES FOR MORE INFO ON FILES 14&15
       C
       C      DATA INPUT ROUTINE
       C
 10    CALL INDATA
       CALL ANGLESIN
       CALL SHRNKEIN
       C
       C      GENERATE NODAL COORDINATES
 15    C
       CALL NODES
       C
       C      GENERATE NODAL/ELEMENT CONNECTIVITY
       CALL ELEMENTS
 20    C
       C      READS AND ASSIGNS ANGLES & ASSIGN MATERIAL PROPERTIES TO
       ELEMENTS
       CALL MATERIAL
       C
 25    C      COMPUTE NUMBER OF EQUATIONS
       NEQ=NUMNOD*NDOF
       IIN=10
       IOUT=16
       C
 30    C      DRAW MESH TO SCREEN
       CALL DRAWSECT
       C
       C      WRITE TO OUTPUT FILE
       CALL DUMP
 35    ENDIF
       C
       2000  FORMAT(1X,'PROGRAM DIMENS - DIMENSIONAL STABILITY
       ANALYSIS',
       1 /,2X,'Do you wish to generate data or perform the analysis?',
 40    2 /,4X,'If ready to run analysis, type "yes"',
       3 /,4X,'If generating data, type "no"')
       2010 FORMAT(1X,'Enter file name with no extension')
       2020 FORMAT(/,1X,'********** PROBLEM SETUP MODE **********')
       2030 FORMAT(/,1X,'********** CONDUCT ANALYSIS MODE **********',
 45    1 /,12X,'USE EXISTING DATA FILE')
       STOP
       END
       SUBROUTINE WSIZER
       C
 50    C           WINDOW SIZER
       C
```

```
      USE MSFLIB
      LOGICAL(4) RESULT
      TYPE (QWINFO) WINFO
      OPEN (10,FILE='USER',TITLE='DIMENS - DIMENSIONAL STABILITY')
   5  C            MAXIMIZE FRAME WINDOW
      WINFO.TYPE=QWIN$MAX
      RESULT=SETWSIZEQQ(QWIN$FRAMEWINDOW, WINFO)
      C            MAXIMIZE CHILD WINDOW
      RESULT=SETWSIZEQQ(10,WINFO)
  10  END
      SUBROUTINE INDATA
      C
      C      GENERATE INPUT DATA
      C
  15  IMPLICIT DOUBLE PRECISION (A-H,O-Z), INTEGER(I-N)

COMMON/BOARD/BODIMY,BODIMX,BODIMZ,YINC,XINC,ZINC,NELX,NELY,
      NELZ
      COMMON/BOARD2/PITH(3,2),RPI(2),BASEE,RFAC,DELMOIST
  20  WRITE(10,700)
      READ(10,*) BODIMX,BODIMY,BODIMZ
      WRITE(10,710)
      READ(10,*) NELX,NELY,NELZ
      YINC=BODIMY/DBLE(REAL(NELY))
  25  XINC=BODIMX/DBLE(REAL(NELX))
      ZINC=BODIMZ/DBLE(REAL(NELZ))
      WRITE(10,720)
      READ(10,*) PITH(1,1),PITH(2,1),PITH(3,1)
      WRITE(10,730)
  30  READ(10,*) PITH(1,2),PITH(2,2),PITH(3,2)
      C             WRITE(10,740)
      C             READ(10,*) RPI(1),RPI(2)
      C             WRITE(10,750)
      C             READ(10,*) BASEE
  35  WRITE(10,760)
      WRITE(10,770)
      READ(10,*) RFAC
      WRITE(10,780)
      READ(10,*) DELMOIST
  40  C
      C    FORMAT STATEMENTS
      C
      700 FORMAT(2X,'Input board dimensions in X, Y, Z directions')
      710 FORMAT(2X,'Input number of elements in X, Y, Z directions')
  45  720   FORMAT(2X,'Input pith location at initial end in',
      1' X, Y, Z coordinates')
      730   FORMAT(2X,'Input pith location at terminating end in',
      1' X, Y, Z coordinates')
      740 FORMAT(2X,'Input rings per inch at initial and terminating end',
  50  1' of board')
      750 FORMAT(2X,'Input base modulus of elasticity for board')
```

```
  760 FORMAT(2X,'Are annual ring widths high and near constant or '/ 3x
 1 'progress from pith, wide to narrow?')
  770 FORMAT(2X,'Input a value between .1 and .1 where .1 = wide and'/
 1 ' constant rings and .4 = wide at pith progressing to narrow')
  780 FORMAT(2X,'Input the change in moisture content for the board')
      RETURN
      END
      SUBROUTINE READIN
      IMPLICIT DOUBLE PRECISION (A-H,O-Z), INTEGER(I-N)
C
      DIMENSION Z1(3),Z2(3),IZ(3)

COMMON/BOARD/BODIMY,BODIMX,BODIMZ,YINC,XINC,ZINC,NELX,NELY,
     NELZ
      COMMON /CPDS/ CORD(3,5000),FEXT(15000),DISP(15000)
      COMMON /ELEM/ KFIX(3,5000),LINK(20,2500),MAT(2500)
      COMMON /KONTRL/ NUMNOD,NDOF,NELE,NNPE,NSD,NEQ,IBAND
      COMMON /MATRL / NMAT,RMAT(9,2500)
      COMMON /SHRINK/ BETAM(3,2500),DELM(2500),EPSNAU(2500,6)
      COMMON /QE/ E(6,6),RA(3,3),ELM(6,6,2500),
     1 PHI(2500),RHO(2500),AMDA(2500),C(6,6)
      COMMON /DEVICE/ IIN,IOUT,IBUG,NGP,IWP,ITP,INP,IEP
C
C       READ IN CONTROL INFORMATION
C
      READ(IIN,*)NUMNOD,NDOF,NELE,NNPE,NSD,NMAT,NGP,IWP,ITP,INP,IEP
      READ(IIN,*)BODIMY,BODIMX,BODIMZ,YINC,XINC,ZINC,NELX,NELY,NELZ
C
C---- READ AND WRITE NODAL DATA
C
      WRITE(IOUT,2000)
    5 DO 30 I=1,NUMNOD
      READ(IIN,*)N,(Z1(J),J=1,3),(IZ(J),J=1,3),(Z2(J),J=1,3)
      DO 10 J=1,NSD
   10 CORD(J,I)=Z1(J)
      DO 20 J=1,NDOF
      IF(IZ(J).EQ.0) KFIX(J,I)=1
      IF(IZ(J).EQ.1) KFIX(J,I)=0
      IF(IZ(J).EQ.2) KFIX(J,I)=2
   20 FEXT((I-1)*NDOF+J)=Z2(J)
      WRITE(IOUT,2001)N,(Z1(J),J=1,3),(IZ(J),J=1,3),(Z2(J),J=1,3)
   30 CONTINUE
C
C---- READ AND WRITE ELEMENT DATA
C
      WRITE(IOUT,2002)
      DO 40 I=1,NELE
      READ(IIN,*)N,MAT(I),(LINK(J,I),J=1,NNPE)
      WRITE(IOUT,2003)N,MAT(I),(LINK(J,I),J=1,NNPE)
   40 CONTINUE
C
```

```
      C---- READ AND WRITE MATERIAL DATA
      C
      WRITE(IOUT,2004)
      DO 50 I=1,NMAT
    5 READ(IIN,*) N,(RMAT(J,I),J=1,9)
      READ(IIN,*) ALPHAD,BETAD,GAMMAD,BETAM(1,I),BETAM(2,I),BETAM(3,I),
     1 DELM(I)
      WRITE(IOUT,2005)N,(RMAT(J,I),J=1,9),ALPHAD,BETAD,GAMMAD,
     1   BETAM(1,I),BETAM(2,I),BETAM(3,I),DELM(I)
   10 C
      XCORD=0.0
      YCORD=0.0
      ZCORD=0.0
      C          DO 55 ASSUMES NMAT=NUMBER OF ELEMENTS
   15 C          THIS IS TO STORE GRAIN ANGLES TO FILE FOR LATER
      ANALYSIS
      DO 55 J=1,8
      XCORD=XCORD+CORD(1,LINK(J,I))
      YCORD=YCORD+CORD(2,LINK(J,I))
   20 ZCORD=ZCORD+CORD(3,LINK(J,I))
      55 CONTINUE
      XCORD=XCORD/8.0
      YCORD=YCORD/8.0
      ZCORD=ZCORD/8.0
   25 WRITE(11,2500) ALPHAD,BETAD,GAMMAD,XCORD,YCORD,ZCORD
      CALL ANGLECON(I,ALPHAD,BETAD,GAMMAD)
      50 CONTINUE
      C
      C
   30 100 WRITE(IOUT,3000)
      RETURN
      1000 FORMAT(I5,3F20.0,2X,3I1/3F20.0)
      1001 FORMAT(16I5/16I5)
      1002 FORMAT(I5,5F15.0/5F15.0)
   35 1003 FORMAT(3F10.0)
      2000 FORMAT(///,40H NODAL DATA  (#,X,Y,Z,KX,KY,KZ,FX,FY,FZ),/,
     1X,10(1H-))
      2001 FORMAT(I5,3f10.2,3I3,1X,3f10.2)
      2002 FORMAT(///,33H ELEMENT DATA  (#,MAT#,N1,N2,...),/,1X,12(1H-))
   40 2003 FORMAT(2I5/20I5)
      2004 FORMAT(///,35H MATERIAL DATA  (#,RMAT1,RMAT2,...),/,1X,13(1H-))
      2005 FORMAT(I3,9E12.4/3X,3F10.2,1X,3F10.5,1X,F8.1)
      2500 FORMAT(2X,3F9.3,3F8.2)
      3000 FORMAT(/)
   45 END
      SUBROUTINE NODES
      IMPLICIT DOUBLE PRECISION (A-H,O-Z), INTEGER(I-N)
      COMMON/KONTRL/NUMNOD,NDOF,NELE,NNPE,NSD,NEQ,IBAND
      COMMON/LIMITS/MAXELE,MAXNOD
   50 COMMON/CPDS/CORD(3,5000),FEXT(15000),disp(15000)
      COMMON/ELEM/KFIX(3,5000),LINK(20,2500),MAT(2500)
```

DPP:SDY:JOC:ejk:dm  9/2/99  1574-53412  Ref. No. 22886   EXPRESS MAIL LABEL NO. EL121365070US
                                                          Date of Deposit: September 2, 1999
-27-

```
         COMMON/BOARD/BODIMY,BODIMX,BODIMZ,YINC,XINC,ZINC,NELX,NELY,
         NELZ
         C
         C    ESTABLISH NODAL COORDINATES
 5       C
         C    SET INITIAL VALUES
         C
         NODNUM=0
         NX=1
10       NY=2
         NZ=3
         DO 180 I=1,NELZ+1
         ZLOC=(I-1)*ZINC
         DO 120 J=1,NELX
15       YLOC=YINC*(-.5)
         XLOC=(J-1)*XINC
         DO 100 K=1,NELY
         C
         C    BEGINNING COLUMN EDGE
20       C
         IF(NODNUM.GT.MAXNOD) CALL ERROR(1,MAXNOD)
         NODNUM=NODNUM+1
         YLOC=YINC*.5+YLOC
         CORD(NY,NODNUM)=YLOC
25       CORD(NX,NODNUM)=XLOC
         CORD(NZ,NODNUM)=ZLOC
         NODNUM=NODNUM+1
         YLOC=YINC*.5+CORD(NY,NODNUM-1)
         CORD(NY,NODNUM)=YLOC
30       CORD(NX,NODNUM)=XLOC
         CORD(NZ,NODNUM)=ZLOC
         100   CONTINUE
         NODNUM=NODNUM+1
         YLOC=YINC*.5+CORD(NY,NODNUM-1)
35       CORD(NY,NODNUM)=YLOC
         CORD(NX,NODNUM)=XLOC
         CORD(NZ,NODNUM)=ZLOC
         C
         C    MIDNODE COLUMN
40       C
         XLOC=XINC*.5+XLOC
         DO 110 L=1,NELY
         NODNUM=NODNUM+1
         YLOC=(L-1)*YINC
45       CORD(NY,NODNUM)=YLOC
         CORD(NX,NODNUM)=XLOC
         CORD(NZ,NODNUM)=ZLOC
         110   CONTINUE
         NODNUM=NODNUM+1
50       CORD(NY,NODNUM)=BODIMY
         CORD(NX,NODNUM)=XLOC
```

```
           CORD(NZ,NODNUM)=ZLOC
           120 CONTINUE
           C
           C    END COLUMN
     5     C
           XLOC=BODIMX
           YLOC=YINC*(-.5)
           DO 130 K=1,NELY
           NODNUM=NODNUM+1
    10     YLOC=YINC*.5+YLOC
           CORD(NY,NODNUM)=YLOC
           CORD(NX,NODNUM)=XLOC
           CORD(NZ,NODNUM)=ZLOC
           NODNUM=NODNUM+1
    15     YLOC=YINC*.5+CORD(NY,NODNUM-1)
           CORD(NY,NODNUM)=YLOC
           CORD(NX,NODNUM)=XLOC
           CORD(NZ,NODNUM)=ZLOC
           130 CONTINUE
    20     NODNUM=NODNUM+1
           YLOC=YINC*.5+CORD(NY,NODNUM-1)
           CORD(NY,NODNUM)=YLOC
           CORD(NX,NODNUM)=XLOC
           CORD(NZ,NODNUM)=ZLOC
    25     C
           C    MIDELEMENT SWATH
           C
           C    SKIP IF FAR Z END OF BOARD
           IF(I.EQ.(NELZ+1)) GOTO 180
    30     C
           XLOC=-XINC
           ZLOC=ZLOC+.5*ZINC
           DO 150 J=1,NELX+1
           XLOC=XINC+XLOC
    35     DO 140 K=1,NELY+1
           IF(NODNUM.GT.MAXNOD) CALL ERROR(1,MAXNOD)
           NODNUM=NODNUM+1
           YLOC=(K-1)*YINC
           CORD(NY,NODNUM)=YLOC
    40     CORD(NX,NODNUM)=XLOC
           CORD(NZ,NODNUM)=ZLOC
           140    CONTINUE
           YLOC=BODIMY
           CORD(NY,NODNUM)=YLOC
    45     CORD(NX,NODNUM)=XLOC
           CORD(NZ,NODNUM)=ZLOC
           150 CONTINUE
           180 CONTINUE
           NUMNOD=NODNUM
    50     C
           C       INITIALIZE BOUNDARY CONDITION AND NODAL LOAD ARRAYS
```

```
      ICOUNT=0
      DO 200 I=1,NUMNOD
      DO 200 J=1,3
      ICOUNT=ICOUNT+1
    5 FEXT(ICOUNT)=0.0
      KFIX(J,I)=0
  200 CONTINUE
      RETURN
      END
   10 SUBROUTINE ELEMENTS
      IMPLICIT DOUBLE PRECISION (A-H,O-Z), INTEGER(I-N)
      COMMON/KONTRL/NUMNOD,NDOF,NELE,NNPE,NSD,NEQ,IBAND
      COMMON/LIMITS/MAXELE,MAXNOD
      COMMON/ELEM/KFIX(3,5000),LINK(20,2500),MAT(2500)
   15
      COMMON/BOARD/BODIMY,BODIMX,BODIMZ,YINC,XINC,ZINC,NELX,NELY,
      NELZ
      C
      C     ESTABLISH NODAL/ELEMENT LINKAGE IN LINK
   20 C
      C     CHECK LIMITS
      C
      NELE=NELX*NELY*NELZ
      IF(NELE.GT.MAXELE) CALL ERROR(2,MAXELE)
   25 C
      NODNUM=0
      NELENUM=0
      NODSTOR2=(NELY*2+1)*(NELX+1)+(NELY+1)*NELX
      NODSTOR=NODSTOR2+(NELY+1)*(NELX+1)
   30 NODMIDB=0
      DO 130 I=1,NELZ
      NODBEG=(I-1)*NODSTOR-NELY-3
      DO 120 J=1,NELX
      NODBEG=NODBEG+NELY+2
   35 NODMIDB=(1-J)*(2*(NELY)+1)
      DO 110 K=1,NELY
      NELENUM=NELENUM+1
      NODBEG=NODBEG+2
      NODBACK=NODBEG+NODSTOR
   40 NODMID=NODBEG+NODSTOR2+NODMIDB
      LINK(1,NELENUM)=NODBACK+NELY*3+4
      LINK(2,NELENUM)=NODBACK+NELY*3+2
      LINK(3,NELENUM)=NODBEG+NELY*3+2
      LINK(4,NELENUM)=LINK(3,NELENUM)+2
   45 LINK(5,NELENUM)=NODBACK+2
      LINK(6,NELENUM)=NODBACK
      LINK(7,NELENUM)=NODBEG
      LINK(8,NELENUM)=NODBEG+2
      LINK(9,NELENUM)=NODBACK+NELY*3+3
   50 LINK(10,NELENUM)=NODMID+NELY+2-K
      LINK(11,NELENUM)=LINK(3,NELENUM)+1
```

```
         LINK(12,NELENUM)=LINK(10,NELENUM)+1
         LINK(13,NELENUM)=NODBACK+1
         LINK(14,NELENUM)=NODMID+1-K
         LINK(15,NELENUM)=NODBEG+1
    5    LINK(16,NELENUM)=LINK(14,NELENUM)+1
         LINK(17,NELENUM)=NODBACK+NELY*2+3-K
         LINK(18,NELENUM)=LINK(17,NELENUM)-1
         LINK(19,NELENUM)=NODBEG+NELY*2+2-K
         LINK(20,NELENUM)=LINK(19,NELENUM)+1
   10 110 CONTINUE
      120 CONTINUE
      130 CONTINUE
         DO 150 I=1,NELE
         MAT(I)=I
   15 150         CONTINUE
         RETURN
         END
         SUBROUTINE DUMP
         IMPLICIT DOUBLE PRECISION (A-H,O-Z), INTEGER(I-N)
   20    C
         C   PRINT TO FILE MESH INFORMATION
         C
         COMMON/KONTRL/NUMNOD,NDOF,NELE,NNPE,NSD,NEQ,IBAND
         COMMON/CPDS/CORD(3,5000),FEXT(15000),disp(15000)
   25
         COMMON/BOARD/BODIMY,BODIMX,BODIMZ,YINC,XINC,ZINC,NELX,NELY,
         NELZ
         COMMON/ELEM/KFIX(3,5000),LINK(20,2500),MAT(2500)
         COMMON /MATRL / NMAT,RMAT(9,2500)
   30    COMMON /QE/ E(6,6),RA(3,3),ELM(6,6,2500),
            1 PHI(2500),RHO(2500),AMDA(2500),C(6,6)
              COMMON /SHRINK/ BETAM(3,2500),DELM(2500),EPSNAU(2500,6)
              COMMON /DEVICE/ IIN,IOUT,IBUG,NGP,IWP,ITP,INP,IEP
         C
   35    C      WRITE CONTROL INFORMATION
         C WRITE(IOUT,2000)NUMNOD,NDOF,NELE,NNPE,NSD,NMAT,NGP,IWP,ITP,INP,I
         EP
   40    WRITE(IOUT,2006)BODIMY,BODIMX,BODIMZ,YINC,XINC,ZINC,NELX,NELY,N
         ELZ
         C
         C---- WRITE NODAL DATA
         C
   45    DO 20 N=1,NUMNOD
         WRITE(IOUT,2001)N,(CORD(J,N),J=1,3),(KFIX(J,N),J=1,3),
              1 FEXT((N)*3-2),FEXT((N)*3-1),FEXT((N)*3)
            20 CONTINUE
         C
   50    C---- WRITE ELEMENT DATA
         C
```

```
         DO 40 I=1,NELE
         WRITE(IOUT,2003)I,MAT(I),(LINK(J,I),J=1,NNPE)
      40 CONTINUE
      C
      C---- WRITE MATERIAL DATA
      C
      C     PRINTING OUT ALPHA, BETA, GAMMA GRAIN ANGLES STORED TEMPORARILY IN
      C              PHI,RHO,AMDA
         DO 50 I=1,NMAT
         WRITE(IOUT,2005)I,(RMAT(J,I),J=1,9)
             WRITE(IOUT,2010)PHI(I),RHO(I),AMDA(I),BETAM(1,I),
       1 BETAM(2,I),BETAM(3,I),DELM(I)
      50 CONTINUE
     100 WRITE(IOUT,3000)
         RETURN
    2000 FORMAT(1X,I5,I3,I5,8I4)
    2001 FORMAT(I5,3F10.2,1X,3I3,1X,3f7.0)
    2003 FORMAT(2I5/20I5)
    2005 FORMAT(I3,9E12.4)
    2006 FORMAT(6F8.1,3I3)
    2010 FORMAT(3F8.3,3F12.8,1X,F8.1)
    3000 FORMAT(/)
         END
      C
      C****************************************************************
      C********          GRAPHICS PORTIONS OF PROGRAM
      C****************************************************************
             SUBROUTINE DRAWSECT
             IMPLICIT DOUBLE PRECISION (A-H,O-Z), INTEGER(I-N)
             CHARACTER*3 ANSWER
             CHARACTER*1 AXIS
             CHARACTER*70 WTITLE
             LOGICAL SHONODNO,SHOW,ANALY

COMMON/VIEW/AXIS,WTITLE,VIEWD,SHONODNO,ANALY,SMAG
      C
             SHOW=.TRUE.
     100     WRITE(10,700)
             READ(10,*) ANSWER
             IF(ANSWER.EQ.'NO'.OR.ANSWER.EQ.'no') SHOW=.FALSE.
                IF(.NOT.SHOW) RETURN
             CLOSE(20)
             SHONODNO=.TRUE.
                WRITE(10,705)
                READ(10,*) ANSWER
                IF(ANSWER.EQ.'NO'.OR.ANSWER.EQ.'no') SHONODNO=.FALSE.
             WRITE(10,710)
             READ (10,*) AXIS
             WRITE(10,720) AXIS
```

```
                    READ(10,*) VIEWD
                    IF(ANALY) THEN
                    WRITE(10,730)
                    READ(10,*) SMAG
 5                  ENDIF
                        IF(VIEWD.LT.0.0) VIEWD=0.0
                        IF(AXIS.EQ.'Z'.OR.AXIS.EQ.'z') CALL ZVIEW
                        IF(AXIS.EQ.'Y'.OR.AXIS.EQ.'y') CALL YVIEW
                        IF(AXIS.EQ.'X'.OR.AXIS.EQ.'x') CALL XVIEW
10                  GO TO 100
            700     FORMAT(/,1X,'Would you like to plot a cross section of the mesh?')
            705 FORMAT(/,1X,'Show node numbers?')
            710     FORMAT(/,2X,'Input the axis you would like to view from',
            1 '(X,Y, or Z)')
15          720     FORMAT(/,2X,'Input the view point from the origin of the',A2,
            1' axis')
            730 FORMAT(/,1X,'Input magnification factor for displacements')
                    RETURN
                    END
20          SUBROUTINE CHARVER(INTE,NUMBER)
            C   THIS SUBROUTINE CONVERTS INTEGER DATA TO CHARACTER DATA
            C
                CHARACTER*4 NUMBER
                CHARACTER CAR(10)
25              DATA CAR/'0','1','2','3','4','5','6','7','8','9'/
            C
                ITH=INTE/1000
                IH=INTE/100-ITH*10
                IT=INTE/10-ITH*100-IH*10
30              IS=INTE-ITH*1000-IH*100-IT*10
            C
                NUMBER = CAR(ITH+1)//CAR(IH+1)//CAR(IT+1)//CAR(IS+1)
                    IF(ITH.EQ.0) NUMBER=CAR(IH+1)//CAR(IT+1)//CAR(IS+1)
                    IF(ITH.EQ.0.AND.IH.EQ.0) NUMBER=CAR(IT+1)//CAR(IS+1)
35                  IF(ITH.EQ.0.AND.IH.EQ.0.AND.IT.EQ.0) NUMBER=CAR(IS+1)
            C
                RETURN
                END 40              SUBROUTINE ZVIEW
                USE MSFLIB
                IMPLICIT DOUBLE PRECISION (A-H,O-Z), INTEGER(I-N)
                INTEGER(2) MAXX,MAXY,STATUS,NODES(8),NODESA(8),NODESB(8)
                INTEGER*4 COLOR
45              CHARACTER*70 WTITLE
                CHARACTER*4 CORDNUMS
                CHARACTER*1 AXIS
                LOGICAL SHONODNO,ANALY
                COMMON/ELEM/KFIX(3,5000),LINK(20,2500),MAT(2500)
50              COMMON/CPDS/CORD(3,5000),FEXT(15000),disp(15000)
```

DPP:SDY:JOC:ejk:dm  9/2/99   1574-53412   Ref. No. 22886    EXPRESS MAIL LABEL NO. EL121365070US
Date of Deposit: September 2, 1999
-33-

```
              COMMON/BOARD/BODIMY,BODIMX,BODIMZ,YINC,XINC,ZINC,NELX,
       NELY,NELZ
              COMMON/SCREEN/ MAXX,MAXY,WCORD(8,2),CORDNUMS(8)
              COMMON/RINGS/ XBEG,XEND,YBEG,YEND
    5         COMMON /QE/ E(6,6),RA(3,3),ELM(6,6,2500),
             1 PHI(2500),RHO(2500),AMDA(2500),C(6,6)
              COMMON/VIEW/AXIS,WTITLE,VIEWD,SHONODNO,ANALY,SMAG
              DATA NODESA/7,15,8,20,4,11,3,19/
              DATA NODESB/6,13,5,17,1,9,2,18/
   10  C

WTITLE='View From Z Axis'
                    CALL GRAPHICSMODE
                    CALL CLEARSCREEN( $GCLEARSCREEN )
   15               SCALER=BODIMX
                    IF(BODIMY.GT.BODIMX) SCALER=BODIMY
                    STATUS = SETWINDOW(.FALSE.,-SCALER*.3,-
       SCALER*.3,SCALER*1.5,
             1      SCALER*1.5)
   20               NELIN=NINT(VIEWD/ZINC)
       C
       C     NEED TO CORRECT FOR VERY LAST X-SECTION OF ELEMENTS
       C
                    IF((NELIN*ZINC).GT.(ZINC*(NELZ-1))) THEN
   25                    NELIN=NELIN-1
                         DO 100 I=1,8
                              NODES(I)=NODESB(I)
          100            CONTINUE
                    ELSE
   30                    DO 110 I=1,8
                              NODES(I)=NODESA(I)
          110            CONTINUE
                    ENDIF
                    NUMEVIEW=NELX*NELY
   35               NUMELE=NUMEVIEW*NELIN
                    NEL=NUMELE
       C
       C      SETUP SCREEN COORDINATES AND DRAW LINES
       C
   40               COLOR=SETCOLORRGB(#000000) !BLACK
                    IF(ANALY) COLOR=SETCOLORRGB(#0000FF) !BRIGHT RED
                    DO 150 I=1,NUMEVIEW
                         NEL=NEL+1
                         XCORD=0.0
   45                    YCORD=0.0
                         DO 120 J=1,8
                              WCORD(J,1)=CORD(1,(LINK(NODES(J),NEL)))
                              WCORD(J,2)=CORD(2,(LINK(NODES(J),NEL)))
                              XCORD=XCORD+WCORD(J,1)
   50                         YCORD=YCORD+WCORD(J,2)
```

```
              IF(SHONODNO) CALL
     CHARVER(LINK(NODES(J),NEL),CORDNUMS(J))
 120          CONTINUE
              CALL DRAWLINES
     C
     C        PLOT RING ANGLES
     C
              XCORD=XCORD/8.0
              YCORD=YCORD/8.0
              YDIM=(WCORD(3,2)-WCORD(1,2))
              XDIM=(WCORD(7,1)-WCORD(1,1))
              YINC=YDIM*.25
              XINC=(DTAND(AMDA(NEL)))*YINC
              IF(ABS(XINC).GT.(XDIM*.5)) THEN
                  XINC=XDIM*.25
                  YINC=XINC/DTAND(AMDA(NEL))
              ENDIF
              XBEG=XCORD+XINC
              YBEG=YCORD-YINC
              XEND=XCORD-XINC
              YEND=YCORD+YINC
              CALL DRAWRING
     C
 150      CONTINUE
          IF(.NOT.ANALY) RETURN
     C
     C        DRAW DEFORMED SHAPE
     C
              COLOR=SETCOLORRGB(#000000)  !Black
              SHONODNO=.FALSE.
              NEL=NUMELE
              DO 220 I=1,NUMEVIEW
                  NEL=NEL+1
                  DO 200 J=1,8
                      WCORD(J,1)=CORD(1,(LINK(NODES(J),NEL)))+
     1                    SMAG*(DISP((3*LINK(NODES(J),NEL))-2))
                      WCORD(J,2)=CORD(2,(LINK(NODES(J),NEL)))+
     1                    SMAG*(DISP((3*LINK(NODES(J),NEL))-1))
 200              CONTINUE
                  CALL DRAWLINES
 220      CONTINUE
     C
          END
          SUBROUTINE XVIEW
          USE MSFLIB
          IMPLICIT DOUBLE PRECISION (A-H,O-Z), INTEGER(I-N)
          INTEGER(2) MAXX,MAXY,STATUS,NODES(8),NODESA(8),NODESB(8)
          CHARACTER*70 WTITLE
          CHARACTER*4 CORDNUMS
          CHARACTER*1 AXIS
          LOGICAL SHONODNO,ANALY
```

```
        COMMON/ELEM/KFIX(3,5000),LINK(20,2500),MAT(2500)
        COMMON/CPDS/CORD(3,5000),FEXT(15000),disp(15000)
        COMMON/BOARD/BODIMY,BODIMX,BODIMZ,YINC,XINC,ZINC,NELX,
   NELY,NELZ
 5      COMMON/SCREEN/ MAXX,MAXY,WCORD(8,2),CORDNUMS(8)
        COMMON/VIEW/AXIS,WTITLE,VIEWD,SHONODNO,ANALY,SMAG
        DATA NODESA/6,14,7,15,8,16,5,13/
        DATA NODESB/2,10,3,11,4,12,1,9/
   C
10              WTITLE='View From X Axis'
                CALL GRAPHICSMODE
                CALL CLEARSCREEN( $GCLEARSCREEN )
                SCALER=BODIMZ
                IF(BODIMY.GT.BODIMZ) SCALER=BODIMY
15              STATUS = SETWINDOW(.FALSE.,-SCALER*.1,-
   SCALER*.1,SCALER*1.2,
        1   SCALER*1.2)
                NELIN=NINT(VIEWD/XINC)
                NUMEVIEW=NELZ*NELY
20 C
   C    NEED TO CORRECT FOR VERY LAST X-SECTION OF ELEMENTS
   C
                IF((NELIN*XINC).GT.(XINC*(NELX-1))) THEN
                        NELIN=NELIN-1
25                      DO 100 I=1,8
                                NODES(I)=NODESB(I)
        100             CONTINUE
                ELSE
                        DO 110 I=1,8
30                              NODES(I)=NODESA(I)
        110             CONTINUE
                ENDIF
   C
   C    SETUP SCREEN COORDINATES AND DRAW LINES
35 C
                DO 160 K=1,NELZ
                        NEL=NELIN*NELY
                        NEL=NEL+(K-1)*(NELY*NELX)
                DO 150 I=1,NELY
40                      NEL=NEL+1
                DO 120 J=1,8
                        WCORD(J,1)=CORD(2,(LINK(NODES(J),NEL)))
                        WCORD(J,2)=CORD(3,(LINK(NODES(J),NEL)))
                IF(SHONODNO) CALL
45 CHARVER(LINK(NODES(J),NEL),CORDNUMS(J))
        120             CONTINUE
   C
                        CALL DRAWLINES
        150     CONTINUE
50      160     CONTINUE
                IF(.NOT.ANALY) RETURN
```

```
C
C              DRAW DEFORMED SHAPE
C
               COLOR=SETCOLORRGB(#0000FF) !BRIGHT RED
5              SHONODNO=.FALSE.
               DO 230 K=1,NELZ
                   NEL=NELIN*NELY
                   NEL=NEL+(K-1)*(NELY*NELX)
                   DO 220 I=1,NELY
10                     NEL=NEL+1
                       DO 200 J=1,8
                           WCORD(J,1)=CORD(2,(LINK(NODES(J),NEL)))+
     1                     SMAG*(DISP((3*LINK(NODES(J),NEL))-1))
                           WCORD(J,2)=CORD(3,(LINK(NODES(J),NEL)))+
15   1                     SMAG*(DISP((3*LINK(NODES(J),NEL))))
200                    CONTINUE
                       CALL DRAWLINES
220                CONTINUE
230            CONTINUE
20   C
               END
               SUBROUTINE YVIEW
               USE MSFLIB
               IMPLICIT DOUBLE PRECISION (A-H,O-Z), INTEGER(I-N)
25             INTEGER(2) MAXX,MAXY,STATUS,NODES(8),NODESA(8),NODESB(8)
               CHARACTER*70 WTITLE
               CHARACTER*1 AXIS
               CHARACTER*4 CORDNUMS
               LOGICAL SHONODNO,ANALY
30             COMMON/ELEM/KFIX(3,5000),LINK(20,2500),MAT(2500)
               COMMON/CPDS/CORD(3,5000),FEXT(15000),disp(15000)
               COMMON/BOARD/BODIMY,BODIMX,BODIMZ,YINC,XINC,ZINC,NELX,
     NELY,NELZ
               COMMON/SCREEN/ MAXX,MAXY,WCORD(8,2),CORDNUMS(8)
35             COMMON/VIEW/AXIS,WTITLE,VIEWD,SHONODNO,ANALY,SMAG
               DATA NODESA/2,18,6,14,7,19,3,10/
               DATA NODESB/1,17,5,16,8,20,4,12/
     C
               WTITLE='View From Y Axis'
40             CALL GRAPHICSMODE
               CALL CLEARSCREEN( $GCLEARSCREEN )
               SCALER=BODIMX
               IF(BODIMZ.GT.BODIMX) SCALER=BODIMZ
               STATUS = SETWINDOW(.TRUE.,-SCALER*.1,-
45   SCALER*.1,SCALER*1.2,
     1   SCALER*1.2)
               NELIN=NINT(VIEWD/YINC)
     C
     C     NEED TO CORRECT FOR VERY LAST X-SECTION OF ELEMENTS
50   C
               IF((NELIN*YINC).GT.(YINC*(NELY-1))) THEN
```

```
                        NELIN=NELIN-1
                        DO 100 I=1,8
                              NODES(I)=NODESB(I)
        100         CONTINUE
                ELSE
                        DO 110 I=1,8
                              NODES(I)=NODESA(I)
        110         CONTINUE
                ENDIF
      C
      C         SETUP SCREEN COORDINATES AND DRAW LINES
      C
                COLOR=SETCOLORRGB(#000000) !BLACK
                IF(ANALY) COLOR=SETCOLORRGB(#0000FF) !BRIGHT RED
                NEL=1-NELY+NELIN
                DO 160 K=1,NELZ
                DO 150 I=1,NELX
                        NEL=NEL+NELY
                        DO 120 J=1,8
                              WCORD(J,1)=CORD(1,(LINK(NODES(J),NEL)))
                              WCORD(J,2)=CORD(3,(LINK(NODES(J),NEL)))
                              IF(SHONODNO) CALL
      CHARVER(LINK(NODES(J),NEL),CORDNUMS(J))
        120         CONTINUE
      C
                        CALL DRAWLINES
        150     CONTINUE
        160     CONTINUE
                IF(.NOT.ANALY) RETURN
      C
      C         DRAW DEFORMED SHAPE
      C
                COLOR=SETCOLORRGB(#000000) !BLACK
                SHONODNO=.FALSE.
                NEL=1-NELY+NELIN
                DO 230 K=1,NELZ
                DO 220 I=1,NELX
                        NEL=NEL+NELY
                        DO 200 J=1,8
                              WCORD(J,1)=CORD(1,(LINK(NODES(J),NEL)))+
             1                SMAG*(DISP((3*LINK(NODES(J),NEL))-2))
                              WCORD(J,2)=CORD(3,(LINK(NODES(J),NEL)))+
             1                          SMAG*(DISP((3*LINK(NODES(J),NEL))))
        200         CONTINUE
                        CALL DRAWLINES
        220     CONTINUE
        230     CONTINUE
      C
                END
                SUBROUTINE GRAPHICSMODE()
                USE MSFLIB
```

```
                IMPLICIT DOUBLE PRECISION (A-H,O-Z), INTEGER(I-N)
                LOGICAL          STATUSMODE
                INTEGER(2)   MAXX, MAXY, NUMFONTS, INDEX
                INTEGER(4)   BKCOLOR,COLOR
 5              CHARACTER*1 AXIS
                CHARACTER*4 CORDNUMS
                CHARACTER*70 WTITLE
                LOGICAL SHONODNO,ANALY
                TYPE (WINDOWCONFIG)     MYSCREEN
10              TYPE (QWINFO) WINFO
                COMMON/SCREEN/ MAXX,MAXY,WCORD(8,2),CORDNUMS(8)

COMMON/VIEW/AXIS,WTITLE,VIEWD,SHONODNO,ANALY,SMAG
                OPEN (20,FILE='USER',TITLE=WTITLE)
15     C     SET HIGHEST RESOLUTION GRAPHICS MODE
                MYSCREEN.NUMXPIXELS=-1
                MYSCREEN.NUMYPIXELS=-1
                MYSCREEN.NUMTEXTCOLS=-1
                MYSCREEN.NUMTEXTROWS=-1
20              MYSCREEN.NUMCOLORS=-1
                MYSCREEN.FONTSIZE=-1
                MYSCREEN.TITLE=WTITLE
       C
                STATUSMODE=SETWINDOWCONFIG(MYSCREEN)
25              WINFO.TYPE=QWIN$MAX
                RESULT=SETWSIZEQQ(20, WINFO)
       C
       C        DETERMINE THE MAXIMUM DIMENSIONS
       C
30              STATUSMODE=GETWINDOWCONFIG(MYSCREEN)
                MAXX=MYSCREEN.NUMXPIXELS - 1
                MAXY=MYSCREEN.NUMYPIXELS - 1
       C
       C        SET COLOR OPTIONS
35     C
                BKCOLOR=SETBKCOLORRGB(#FFFFFF)
                COLOR=SETCOLORRGB(#000000)   !BLACK
       C
       C        SET FONT OPTIONS
40     C
                NUMFONTS = INITIALIZEFONTS ()
                INDEX = SETFONT('t''Arial''h14p')
             END
             SUBROUTINE DRAWLINES
45              USE MSFLIB
                IMPLICIT DOUBLE PRECISION (A-H,O-Z), INTEGER(I-N)
                CHARACTER*1 AXIS
                CHARACTER*70 WTITLE
                CHARACTER*4 CORDNUMS
50              INTEGER*2 MAXX,MAXY
                LOGICAL SHONODNO,ANALY
```

```
            TYPE (WXYCOORD) WXY
            COMMON/SCREEN/ MAXX,MAXY,WCORD(8,2),CORDNUMS(8)

COMMON/VIEW/AXIS,WTITLE,VIEWD,SHONODNO,ANALY,SMAG
            CALL MOVETO_W(WCORD(1,1)+0.05,WCORD(1,2),WXY)
            IF(SHONODNO) CALL OUTGTEXT(CORDNUMS(1))
            CALL MOVETO_W(WCORD(1,1),WCORD(1,2),WXY)
            DO 100 I=2,8
                STATUS = LINETO_W(WCORD(I,1),WCORD(I,2))
                IF(SHONODNO) THEN
                    CALL MOVETO_W(WCORD(I,1)+0.05,WCORD(I,2),WXY)
                    CALL OUTGTEXT(CORDNUMS(I))
                    CALL MOVETO_W(WCORD(I,1),WCORD(I,2),WXY)
                ENDIF
100         CONTINUE
            STATUS = LINETO_W(WCORD(1,1),WCORD(1,2))
            END
            SUBROUTINE DRAWRING
            USE MSFLIB
            IMPLICIT DOUBLE PRECISION (A-H,O-Z), INTEGER(I-N)
            TYPE (WXYCOORD) WXY
            COMMON/RINGS/ XBEG,XEND,YBEG,YEND
            CALL MOVETO_W(XBEG,YBEG,WXY)
            STATUS = LINETO_W(XEND,YEND)
            END
C
C***************** END OF GRAPHICS ******************************
C
            SUBROUTINE ERROR(IERROR,JERROR)
            IMPLICIT DOUBLE PRECISION (A-H,O-Z), INTEGER(I-N)
            WRITE(10,700)
            WRITE(16,700)
700         FORMAT(/,'** FATAL PROGRAM ERROR **'/)
            GOTO (10,20,30,40,50,60,70,80,90,100) IERROR
C
10          WRITE(10,710) JERROR
            WRITE(16,710) JERROR
710         FORMAT(2X,'NUMBER OF NODES =',I8,' EXCEEDS DIMENSION')
            STOP
20          WRITE(10,720) JERROR
            WRITE(16,720) JERROR
720         FORMAT(2X,'NUMBER OF ELEMENTS =',I8,' EXCEEDS DIMENSION')
            STOP
30          WRITE(10,730) JERROR
            WRITE(16,730) JERROR
730         FORMAT(2X,'BAND WIDTH =',I4,' EXCEEDS DIMENSION')
            STOP
40          WRITE(10,740) JERROR
            WRITE(16,740) JERROR
```

DPP:SDY:JOC:ejk:dm  9/2/99  1574-53412  Ref. No. 22886    EXPRESS MAIL LABEL NO. EL121365070US
Date of Deposit: September 2, 1999
-40-

```
740         FORMAT(2X,'LENGTH OF PITH =',I3,1X,'(INTEGER VALUE)')
            STOP
 50         WRITE(10,750) JERROR
            WRITE(16,750) JERROR
750         FORMAT(2X,'DISTANCE TO PITH =',I3,1X,'(INTEGER VALUE)')
            STOP
 60         WRITE(10,760)
            WRITE(16,760)
760         FORMAT(2X,'CHECK GRAIN ANGLE DATA FILES')
            STOP
 70         WRITE(10,770) JERROR
            WRITE(16,770) JERROR
770         FORMAT(2X, 'ERROR IN GRAIN ANGLE INTERPOLATION ',
     'ROUTINE AT POINT ',I5)
            STOP
 80    WRITE(10,780) JERROR
            WRITE(16,780) JERROR
780         FORMAT(2X, 'LONGINTUDINAL E IS < 0.0 FOR ELEMENT',I4)
            STOP
 90         WRITE(10,790)
            WRITE(16,790)
790         FORMAT(2X, 'ERROR IN CALIBRATE, EINTRCPT<0'/
     1   2X,' RINGS ARE TOO WIDE FOR THIS DISTANCE FROM THE PITH')
            STOP
100         WRITE(10,800)
            WRITE(16,800)
800         FORMAT(2X, 'NUMBER OF DATA POINTS IN LSE FILE
     EXCEEDS'/
     1   2X,'DIMENSION OF 200, NO.OF PTS =',I4)
            STOP
            RETURN
       END
C      ********************************************************
       SUBROUTINE TIMIT
C      ********************************************************
       USE MSFLIB
       IMPLICIT DOUBLE PRECISION (A-H,O-Z)
C
       INTEGER*2 IHR,IDAY,IMIN,IMON,IYR,ISEC,I100TH
       COMMON/INTR/IHR,IDAY,IMIN,IMON,IYR,ISEC,I100TH
C
C
       TIME1=IMIN*60+ISEC+I100TH/100
       CALL GETTIM(ihr,imin,isec,i100th)
       TIME2=IMIN*60+ISEC+I100TH/100
       TIME2=TIME2-TIME1
       WRITE(10,500) TIME2
   500 FORMAT(5X,'EXECUTION TIME=',F10.2,' SECONDS')
       RETURN
       END
```

We claim:

1. A method for determining twist potential of wood, comprising:

nondestructively obtaining plural grain angles of wood; and determining twist potential of the wood based on differences between grain angles.

2. The method according to claim 1 where the wood is lumber.

3. The method according to claim 2 where the lumber comprises a board having major planar surfaces, the method further including obtaining grain angles from at least one major planar surface of the board.

4. The method according to claim 1 where obtaining plural grain angles comprises measuring at least one grain angle.

5. The method according to claim 4 where obtaining plural grain angles comprises measuring plural grain angles.

6. The method according to claim 1 further comprising obtaining at least one dive angle.

7. The method according to claim 1 where plural grain angles are obtained at measuring locations separated by a predetermined distance.

8. The method according to claim 7 where the wood is a board and the grain angles are obtained at substantially one-foot intervals along the board.

9. The method according to claim 8 where the measuring locations are on at least one major planar surface of the board.

10. The method according to claim 1 where the grain angles are obtained using infrared radiation, microwave radiation, light energy, electricity, ultrasound energy, or combinations thereof.

11. The method according to claim 10 where grain angles are obtained using a laser.

12. The method according to claim 10 where grain angle is determined using ultrasound energy.

13. The method according to claim 12, further comprising:

providing a board having first and second faces, first and second edges, and first and second ends;

determining a first transmission speed of an ultrasound pulse through the board along a first path;

determining a second transmission speed of an ultrasound pulse through the board along a second path; and determining grain angle by comparing the first and second transmission speeds.

14. The method according to claim 13 comprising determining plural ultrasound transmission speeds to determine plural grain angles.

15. The method according to claim 14 where grain angles are determined along a longitudinal axis of the board.

16. The method according to claim 1 comprising determining twist potential using a computer.

17. The method according to claim 1 where twist potential is correlated to actual empirically determined twist angle with an $R^2$ value of at least 0.50.

18. A method for determining twist potential in wood, comprising:

providing a piece of wood;

imparting energy to the piece of wood to determine plural grain angles; and determining twist potential of the piece of wood from differences between grain angles.

19. The method according to claim 18 where the piece of wood comprises lumber.

20. The method according to claim 18 where the energy is selected from the group consisting of electromagnetic energy, acoustic energy, and combinations thereof.

21. The method according to claim 20 where electromagnetic energy is provided by a laser.

22. The method according to claim 20 where acoustic energy is ultrasonic energy.

23. The method according to claim 22 where energy is imparted to the wood using an ultrasound device having first and second transducers, the ultrasound energy passing from the first transducer through the wood to the second transducer.

24. The method according to claim 18 where plural grain angles are determined.

25. The method according to claim 18 where grain angles are determined on at least one major planar surface of the wood.

26. The method according to claim 25 where grain angles are determined at predetermined intervals along the wood.

27. The method according to claim 26 where grain angles are determined at regularly spaced intervals along the wood.

28. The method according to claim 18 where twist potential is determined using a computer.

29. The method according to claim 18 where grain angles are determined nondestructively.

30. A non-destructive method for determining twist potential of wood, comprising:

obtaining grain angles of wood at plural measuring locations along the wood; and determining twist potential of the wood based on differences between the grain angles.

31. The method according to claim 30 where twist potential is determined using a finite element model.

32. The method according to claim 31 where wood further comprises a piece of lumber having first and second edges.

33. The method according to claim 31 where the twist potential is determined using the formula Twist potential=$K[\overline{SA_1}-\overline{SA_2}]$, where k is a proportionality constant dependent on dimensions of the wood and $SA_i$ is the average surface grain angle along edge i.

* * * * *